United States Patent
Kim et al.

(10) Patent No.: US 7,838,505 B2
(45) Date of Patent: Nov. 23, 2010

(54) HYBRID HEPATOCYTE GROWTH FACTOR GENE HAVING HIGH EXPRESSION EFFICIENCY OF TWO HETEROTYPES OF HEPATOCYTE GROWTH FACTOR

(75) Inventors: Jong-Mook Kim, Seoul (KR); Woong Hahn, Seoul (KR)

(73) Assignee: ViroMed Co., Ltd. (KR)

( * ) Notice: Subject to any disclaimer, the term of this patent is extended or adjusted under 35 U.S.C. 154(b) by 282 days.

(21) Appl. No.: 11/957,170

(22) Filed: Dec. 14, 2007

(65) Prior Publication Data

US 2009/0131350 A1 May 21, 2009

Related U.S. Application Data

(60) Division of application No. 10/944,277, filed on Sep. 20, 2004, which is a continuation of application No. PCT/KR03/00548, filed on Mar. 20, 2003.

(30) Foreign Application Priority Data

Mar. 20, 2002 (KR) ...................... 10-2002-0015074

(51) Int. Cl.
*A01N 43/04* (2006.01)
*C12N 15/63* (2006.01)
*C12N 15/85* (2006.01)
*C12N 15/86* (2006.01)
*C12N 1/20* (2006.01)
*C12N 1/19* (2006.01)
*C12N 15/00* (2006.01)
*A61K 48/00* (2006.01)
*A61K 31/70* (2006.01)
*C12P 21/00* (2006.01)

(52) U.S. Cl. .................. 514/44 R; 435/320.1; 435/325; 435/252.3; 435/252.33; 435/254.2; 435/69.1; 435/69.4; 435/70.1; 435/71.1; 536/23.51

(58) Field of Classification Search ................... 514/44, 514/44 R
See application file for complete search history.

(56) References Cited

U.S. PATENT DOCUMENTS

| | | | |
|---|---|---|---|
| 5,328,836 A | 7/1994 | Shima et al. | |
| 5,500,354 A | 3/1996 | Kitamura et al. | |
| 5,580,859 A | 12/1996 | Felgner et al. | |
| 5,587,359 A | 12/1996 | Higashio et al. | |
| 5,652,225 A | 7/1997 | Isner | |
| 5,693,622 A | 12/1997 | Wolff et al. | |
| 6,013,624 A | 1/2000 | Goldberg et al. | |
| 6,121,246 A | 9/2000 | Isner | |
| 6,248,722 B1 | 6/2001 | Morishita et al. | |
| 6,258,787 B1 | 7/2001 | Isner | |
| 6,316,419 B1 | 11/2001 | Leiden et al. | |
| 6,413,942 B1 | 7/2002 | Felgner et al. | |
| 6,498,144 B1 | 12/2002 | Rosen et al. | |
| 6,706,694 B1 | 3/2004 | Felgner et al. | |
| 6,887,477 B1 | 5/2005 | Nagano et al. | |
| 7,285,540 B2 | 10/2007 | Morishita et al. | |
| 2002/0172663 A1 | 11/2002 | Palasis | |
| 2003/0148968 A1 | 8/2003 | Hammond et al. | |
| 2003/0171287 A1 | 9/2003 | Morishita et al. | |
| 2004/0105882 A1 | 6/2004 | Morishita et al. | |
| 2004/0228834 A1 | 11/2004 | Isner et al. | |
| 2005/0079581 A1 | 4/2005 | Kim et al. | |
| 2006/0286072 A1 | 12/2006 | Giordano et al. | |
| 2007/0059288 A1 | 3/2007 | Dinsmore et al. | |
| 2008/0268030 A1 | 10/2008 | Morishita et al. | |
| 2009/0004260 A1 | 1/2009 | Morishita et al. | |
| 2009/0082293 A1 | 3/2009 | Giordano et al. | |
| 2009/0202606 A1 | 8/2009 | Kim et al. | |

FOREIGN PATENT DOCUMENTS

| | | |
|---|---|---|
| JP | 11-246433 | 9/1999 |
| WO | WO 98/50079 A2 | 11/1998 |
| WO | WO 99/45775 A1 | 9/1999 |
| WO | WO 01/34208 A1 | 5/2001 |
| WO | WO 02/089856 A1 | 11/2002 |

OTHER PUBLICATIONS

Romano et al. Stem Cells, 1999, 17:191-202.*
Liu et al, Journal of Controlled Release vol. 78, Issues 1-3, Jan. 17, 2002, pp. 259-266.*
Schmitz et al, Gut. Jan. 2002; 50(1): 130-135.*
Liu, Y., "The human hepatocyte growth factor receptor gene: complete structural organization and promoter characterization," *Gene* 215:159-169, Elsevier/North-Holland (1998).
Miyazawa, K., et al., "Molecular Cloning and Sequence Analysis of cDNA for Human Hepatocyte Growth Factor," Biochem. *Biophys. Res. Commun.* 163:967-973, Academic Press (1989).
Nakamura, T., et al., "Molecular cloning and expression of human hepatocyte growth factor," *Nature* 342:440-443, Nature Publishing Group (1989).
Seki, T., et al., "Isolation and Expression of cDNA for Different Forms of Hepatocyte Growth Factor from Human Leukocyte," *Biochem. Biophys. Res. Commun.* 1 72:321-327, Academic Press (1990).

(Continued)

*Primary Examiner*—Valarie Bertoglio
(74) *Attorney, Agent, or Firm*—Sterne, Kessler, Goldstein & Fox P.L.L.C.

(57) ABSTRACT

The present invention relates to a hybrid Hepatocyte Growth Factor (HGF) gene which is prepared by inserting an inherent or foreign intron between exons 4 and 5 in HGF cDNA, which has a base sequence of SEQ ID NO: 2. The gene has high expression efficiency and simultaneously expresses two heterotypes of HGF and dHGF (deleted variant HGF). Further the gene may be used for treating or preventing ischemic or liver diseases.

20 Claims, 12 Drawing Sheets

OTHER PUBLICATIONS

Seki, T., et al., "Organization of the human hepatocyte growth factor-encoding gene," *Gene* 102:213-219, Elsevier/North-Holland (1991).

Shima, N., et al., "Hepatocyte Growth Factor and its Variant with a Deletion of Five Amino Acids are Distinguishable in their Biological Activity and Tertiary Structure," *Biochem. Biophys. Res. Commun.* 200:808-815, Academic Press (1994).

European Search Report for European Application No. EP 03 74 4561, mailed Apr. 18, 2006, European Patent Office, Munich, Germany.

NCBI Entrez, GenBank Database, Accession No. AC004960, "Homo sapiens PAC clone RP5-1098B1 from 7q11.23-q21, complete sequence," 51 pages (first available 1998).

Ngo et al., in The Protein Folding Problem and Tertiary Structure Prediction, 1994, Merz et al. (ed.), Birkhauser, Boston, MA, pp. 433 and 492-495.

Potrykus. Gene transfer to cereals: an assessment, Biotechnology, 1990, 8(6):535-542.

Office Action for Co-pending U.S. Appl. No. 10/944,277, mailed Jan. 9, 2008.

Deng, et al., "Secretory Expression of the Deleted Variant of Human Hepatocyte Growth Factor (hdHGF) in Pichia pastoris," *Chinese Journal of Biochemistry and Molecular Biology*, 2001, 17:590-594, China Academic Journal Electronic Publishing House, Beijing, China.

Kisselev, L., " Polypeptide Release Factors in Prokaryotes and Eukaryotes: Same Function, Different Structure," *Structure*, 2002, 10, pp. 8-9, Elsevier Science Ltd., Cambridge, Massachusetts, USA.

Rubin, et al., "A broad-spectrum human lung fibroblast-derived mitogen is a variant of hepatocyte growth factor," *Proc. Natl. Acad. Sci. USA*, 1991, 88:415-419, Proceedings of the National Academy of Sciences of the United States of America, 500 5th St., Washington, DC 20001.

Warnecke C. et al., "Efficient transcription of the human angiotensin II type 2 receptor gene requires intronic sequence elements," *Biochemical journal*, 1999, 340 (1), pp. 17-24, Portland Press, Colchester, Great Britain.

Wishart et al., " A Single Mutation Converts a Novel Phosphotyrosine Binding into a Dual-Specificity Phosphatase," *Journal of Biological Chemistry*, 1995, 270 (45), pp. 26782-26785, American Society for Biochemistry and Molecular Biology, Bethesda, MD, USA.

Witkowski et al., "Conversion of a A-Ketoacyl Synthase to a Malonyl Decarboxylase by Replacement of the Active-Site Cysteine with Glutamine," *Biochemistry*, 1999, 38 (36), pp. 11643-11650, American Chemical Society, Washington, DC, USA.

Office Action for Co-Pending U.S. Appl. No. 10/944,277, mailed Feb. 13, 2009.

Notice of Allowance and Fees Due for Co-Pending U.S. Appl. No. 10/944,277, mailed May 29, 2009.

Notice of Allowance and Fees Due for Co-Pending U.S. Appl. No. 10/944,277, mailed Oct. 23, 2009.

Co-Pending U.S. Appl. No. 12/650,860, inventors Kim et al., filed Dec. 31, 2009 (Not Yet Published).

Copy of Notice of Allowance and Fees Due for Co-Pending U.S. Appl. No. 12/650,860, mailed Mar. 10, 2010.

Esp@cenet Database, English language abstract of JP 11-246433 A, published Sep. 14, 1999 (listed as document FP5 on the accompanying form PTO/SB/08A).

* cited by examiner

FIG. 11

HYBRID HEPATOCYTE GROWTH FACTOR GENE HAVING HIGH EXPRESSION EFFICIENCY OF TWO HETEROTYPES OF HEPATOCYTE GROWTH FACTOR

CROSS-REFERENCE TO RELATED APPLICATIONS

This application is a divisional of U.S. application Ser. No. 10/944,277, filed Sep. 20, 2004, now allowed, which is a continuation of International Application No. PCT/KR03/00548, filed Mar. 20, 2003, both of which are herein incorporated by reference.

REFERENCE TO A SEQUENCE LISTING SUBMITTED ELECTRONICALLY VIA EFS-WEB

The content of the electronically submitted sequence listing (Name: sequence listing ascii.txt, Size: 31 kilobytes; and Date of Creation: Dec. 14, 2007) filed herewith the application is incorporated by reference in its entirety.

BACKGROUND OF THE INVENTION

1. Field of the Invention

The present invention relates to a highly efficient hybrid Hepatocyte Growth Factor (HGF) gene which simultaneously expresses two heterotypes of HGF.

2. Related Art

The present invention relates to a hybrid HGF gene prepared by inserting an inherent or foreign intron between exons 4 and 5 in HGF cDNA, which has higher expression efficiency than HGF cDNA and simultaneously expresses two heterotypes of HGF and dHGF (deleted variant HGF).

HGF is a heparin binding glycoprotein called a scatter factor. A gene encoding HGF is located at chromosome 721.1 and comprises 18 exons and 17 introns, having the nucleotide sequence of SEQ ID NO: 1 (Seki T., et al., *Gene* 102:213-219 (1991)). A transcript of about 6 kb is transcribed from the HGF gene, and then, a polypeptide HGF precursor consisting of 728 amino acids is synthesized therefrom. Simultaneously, a polypeptide of dHGF precursor consisting of 723 amino acids is also synthesized by an alternative splicing of the HGF gene. The biologically inactive precursors may be converted into active forms of disulfide-linked heterodimer by protease in serum. In the heterodimers, the alpha chain having a high molecular weight forms four kringle domains and an N-terminal hairpin loop like a preactivated peptide region of plasminogen. The kringle domains of a triple disulfide-bonded loop structure consisting of about 80 amino acids may play an important role in protein-protein interaction. The low molecular weight beta chain forms an inactive serine protease-like domain. dHGF consisting 723 amino acids is a polypeptide with deletion of five amino acids in the 1st kringle domain of the alpha chain, i.e., F, L, P, S and S.

It has been recently reported that both of HGF and dHGF have several biological functions, e.g., promoting the growth and morphogenesis of epithelial cell, melanocyte and endothelial cell. However, they are different in terms of immunological or biological properties.

For example, HGF shows about 20-fold, 10-fold and 2-fold higher activities than dHGF in promoting DNA synthesis in human umbilical cord venous endothelial cell, arterial smooth muscle cell and NSF-60 (murine myeloblast cell), respectively. dHGF shows about 3-fold and 2-fold higher activities than HGF in promoting DNA synthesis of LLC-PK1 (pig kidney epithelial cell), and OK (American opossum kidney epithelial cell) and mouse interstitial cell, respectively. HGF has a 70-fold higher solubility in PBS than dHGF. Several anti-dHGF monoclonal antibodies recognize only dHGF, but not HGF or a reduced form of dHGF, which implies structures of HGF and dHGF are different. Accordingly, the simultaneous synthesis of HGF and dHGF in vivo suggests that they biologically interact with each other (Shima, N. et al., *Biochemical and Biophysical Research Communications* 200:808-815 (1994)).

HGF secreted from mesoderm-derived cells has various biological functions, e.g., 1) inducing epithelial cells into a tubular structure; 2) stimulating vascularization from endothelial cells in vitro and in vivo; 3) regeneration of liver and kidney, owing to its anti-apoptosis activity; 4) organogenesis of kidney, ovary and testis; 5) controlling osteogenesis; 6) stimulating the growth and differentiation of erythroid hematopoietic precursor cells; and 7) axon sprouting of neurons (Stella, M. C. and Comoglio, P. M., *The International Journal of Biochemistry & Cell Biology* 31:1357-1362 (1999)). Based on these various functions, HGF or a gene encoding HGF may be developed as a therapeutic agent for treating ischemic or liver diseases. Actually, in vivo, the HGF may exist as either HGF or dHGF, and therefore, the coexpression of HGF and dHGF is important for maximizing the therapeutic effect. Accordingly, the present inventors have endeavored to develop a hybrid HGF gene which can simultaneously express HGF and dHGF with a high efficiency for gene therapy.

SUMMARY OF THE INVENTION

Accordingly, it is a primary object of the present invention to provide a hybrid HGF gene which simultaneously expresses two heterotypes of HGF.

In accordance with one aspect of the present invention, there is provide the hybrid HGF gene having an inherent or foreign intron is inserted between exons 4 and 5 of HGF cDNA.

It is a another object of the present invention to provide a recombinant vector comprising the hybrid HGF gene and a microorganism transformed with the above vector.

It is a still further object of the present invention to provide a pharmaceutical composition for treating or preventing ischemic or liver diseases, which comprises the HGF gene.

BRIEF DESCRIPTION OF THE DRAWINGS

The above and other objects and features of the present invention will become apparent from the following description of the invention, when taken in conjunction with the accompanying drawings which respectively show:

FIG. 11: cerebral angiogenesis of two groups of rabbits which were subject to administrating pCP and pCP-HGF-X7, respectively,

DETAILED DESCRIPTION OF THE INVENTION

Figure 1:
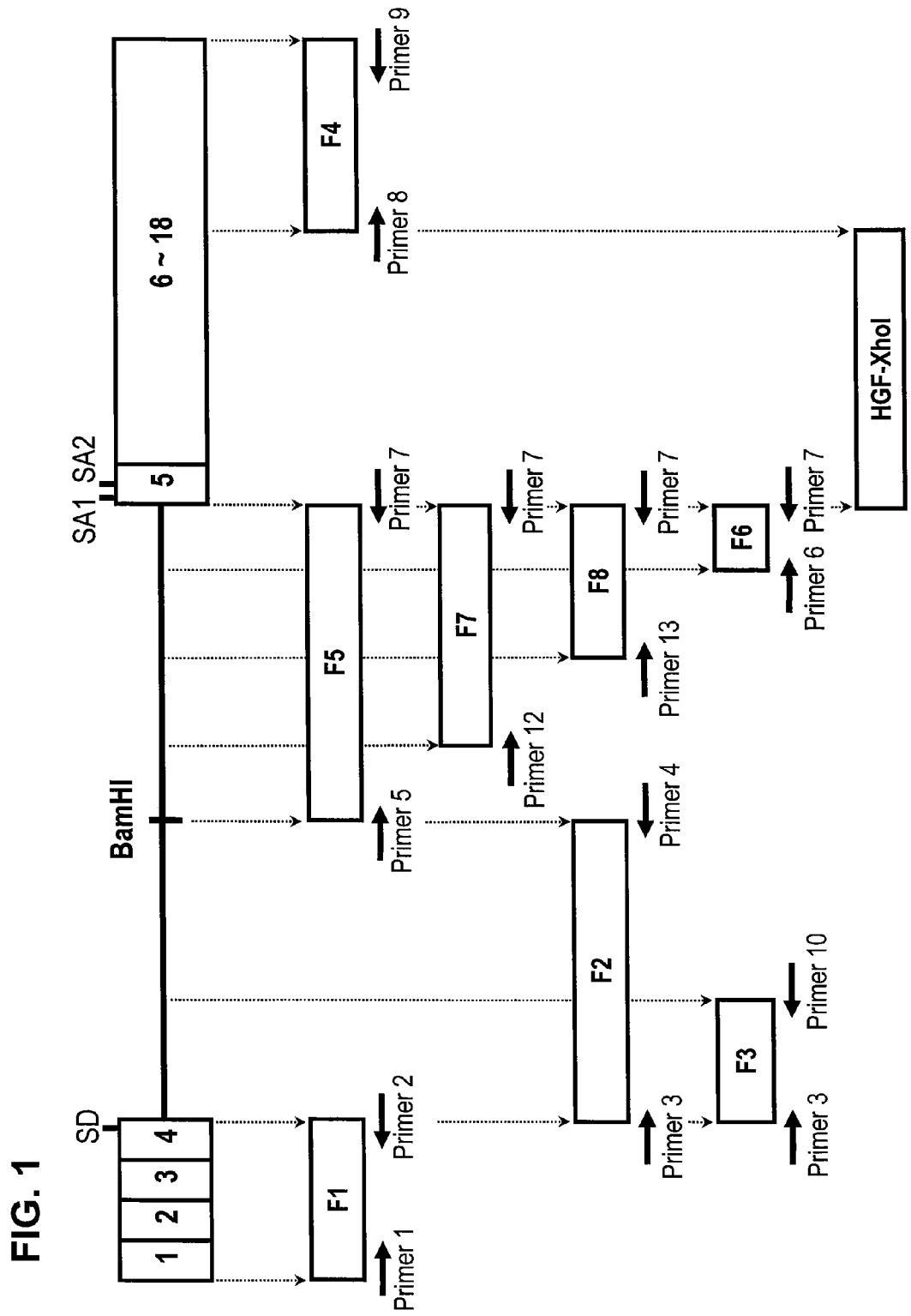
FIG. 1: a schematic diagram of HGF-X prototype illustrating the positions of the gene fragments.

The hybrid Hepatocyte Growth Factor (HGF) gene of the present invention comprises cDNA corresponding to the exons 1 to 18, and an inherent or foreign intron inserted between exons 4 and 5 of the cDNA. The intron comprises a fragment of the inherent intro or a recombinant sequence.

An embodiment of the hybrid HGF gene of the present invention comprising the inherent intron is 7113 bp long and has the nucleotide sequence of SEQ ID NO: 2. The hybrid HGF gene simultaneously expresses both HGF and dHGF, and has higher expression efficiency than HGF cDNA.

Codon degeneracy enables the hybrid HGF gene of the present invention to be modified or changed in the coding and/or non-coding region without altering the amino acid sequence of the protein and the expression of the gene. Accordingly, polynucleotides which is substantially identical to the hybrid HGF gene of SEQ ID NO:2, and the fragments thereof fall within the scope of the invention. "Substantially identical" means that the sequence homology is not less than 80%, preferably not less than 90%, and more preferably not less than 95%.

A hybrid HGF gene may comprise a fragment of inherent intron optionally having a small recombinant sequence inserted thereinto between exons 4 and 5 of HGF cDNA. Herein, such a hybrid HGF gene comprising a fragment of inherent intron designates "HGF-X". HGFX-6, HGF-X7 and HGF-X8 having the nucleotide sequence of SEQ ID Nos: 19 to 21, respectively, are preferred.

The hybrid HGF gene of the present invention is synthesized and inserted into an expression vector, according to the known genetic engineering methods. Then, the vector can be introduced into an appropriate host cells such as *E. coli* and yeast. For example, *Escherichia coli* Top10F' may be transfected with HGF-X7 gene of the present invention. *Escherichia coli* Top10F' pCK-HGFX7 and *Escherichia coli* Top10F' pCP-HGFX7 then obtained were deposited as the accession numbers KCCM-10361 and KCCM-10362, respectively, on Mar. 12, 2002.

By using the transformed cells, the gene of the present invention and the protein encoded thereby may be produced on a large scale.

The vector of the present invention may selectively comprise sequence(s) for regulating gene expression such as promoter or terminator, self-replication sequence and secretory signal, depending on host cells.

Further, the present invention comprises a pharmaceutical compostion for treating or preventing ischemic and liver diseases, which comprises the hybrid HGF gene or the vector comprising the gene as an active ingredient. Preferably, the composition is formulated for injection.

The composition of the present invention may further comprise pharmaceutically acceptable carriers. Any of the conventional procedures in the pharmaceutical field may be used to prepare oral formulations such as tablets, capsules, pills, granules, suspensions and solutions; rejection formulations such as solutions, suspensions, or dried powders that may be mixed with distilled water before injection; locally-applicable formulations such as ointments, creams and lotions; and other formulations.

Carriers generally used in the pharmaceutical field may be employed in the composition of the present invention. For example, orally-administered formulations may include binders, emulsifiers, disintegrating agents, excipients, solubilizing agents, dispersing agents, stabilizing agents, suspending agents, coloring agents or spicery. Injection formulations may comprise preservatives, unagonizing agents, solubilizing agents or stabilizing agents. Preparation for local administration may contain bases, excipients, lubricants or preservatives. Any of the suitable formulations known in the art (Remington's Pharmaceutical Science [the new edition], Mack Publishing Company, Eaton Pa.) may be used in the present invention.

The inventive composition can be clinically administered as various oral and parenteral formulations. A suitable formulation may be prepared using such excipients as additives, enhancers, binders, wetting agents, disintegrating agents and surfactants, or diluents. Solid formulations for oral administration include pills, tablets, dusting powder, granules and capsules. Those solid formulations may be prepared by mixing one or more excipients, e.g. starch, calcium carbonate, sucrose, lactose and gelatin with dibenzylbuthyllacton lignan derivatives. Also, lubricants such as magnesium stearate and talc may be included in the present formulation. Liquid formulations for oral administration include suspension, solution, emulsion and syrup. Those formulations may contain wetting agents, sweeteners, aromatics and preservatives, in addition to general simple diluents such as water and liquid paraffin. Formulations for parenteral administration include sterilized aqueous solution, suspension, emulsion, freeze-dried alternative treatment and suppositories. Water-insoluble excipients and suspending agents comprise vegetable fats such as propylene glycol, polyethylene glycol and olive oil, and injectable esters such as ethyl oleate. Witepsol®, Macrogol®, Tween® 61, cacao fats, laurin fats and glycerogelatins may be used as bases of suppositories.

The inventive composition may be administered orally or via parenteral routes such as intravenous, intramuscular, subcutaneous, intraabdominal, sternal and arterial injection or infusion, or topically through rectal, intranasal, inhalational or intraocular administration.

It should be understood that the typical daily dose of composition of the present invention ought to be determined in light of various relevant factors including the conditions to be treated, the chosen route of administration, the age, sex and body weight of the individual patient, and the severity of the patient's symptom, and can be administrated in a single dose or in divided dose. Therefore, the daily dose should not be construed as a limitation to the scope of the invention in any way.

The following Examples are given for the purpose of illustration only, and are not intended to limit the scope of the invention.

EXAMPLE 1

Preparation of Hybrid Gene Constructs Encoding Human HGF (1) Cloning of HGF Gene Fragments Obtained from Genomic DNA Human HepG2 cells (ATCC Accession NO: HB-8065) were suspended in TES buffer (10 mM Tris-HCl; 1 mM EDTA; 0.7% SDS) and treated with 400 μg/Ml of proteinase K at 50° C. for 1 hour. Subsequently, genomic DNA was extracted from the cell suspension by phenol/chloroform extraction and ethanol precipitation according to the conventional method in the art.

In the PCR amplication, the extracted genomic DNA was employed as a template DNA. As primer pairs, the synthetic nucleotides of SEQ ID NOs: 3and 4 were employed to obtain DNA fragments containing: HGF gene fragment 2 (HGF-F2), SEQ ID NOs: 3 and 5; HGF-F3, SEQ ID NOs: 6 and 7; HGF-F5, SEQ ID NOs: 8 and 7; HGF-F7, SEQ ID NOs: 9 and 7; HGF-F8, SEQ ID NOs: 10 and 7; HGF-F6, respectively (FIG. 1). The PCR amplification mixture was prepared by mixing 1 μl of template DNA, 1 μl each of primer (10 pmol/μl), 10 μl of dNTP (10 mM), 3.5 unit of Expand High Fidelity enzyme (Gibco BRL, USA) and 10 μl of enzyme buffer solution and adjusted to a final volume of 100 μl with distilled water. 30 cycles of the PCR amplification was carried out, each cycle consisting of 1 min at 94° C., 1 min at 55° C. and 30 sec at 72° C. The primers used herein and the amplified gene fragments obtained therefrom are shown in Table 1.

TABLE 1

| 5' primer | 3' primer | Amplified fragment |
|---|---|---|
| gHGF3 (SEQ ID NO: 3) | gHGF4 (SEQ ID NO: 4) | HGF gene fragment 2 (HGF-F2) |
| gHGF3 (SEQ ID NO: 3) | gHGF10 (SEQ ID NO: 5) | HGF gene fragment 3 (HGF-F3) |
| gHGF5 (SEQ ID NO: 6) | gHGF7 (SEQ ID NO: 7) | HGF gene fragment 5 (HGF-F5) |
| gHGF12 (SEQ ID NO: 8) | gHGF7 (SEQ ID NO: 7) | HGF gene fragment 7 (HGF-F7) |
| gHGF13 (SEQ ID NO: 9) | gHGF7 (SEQ ID NO: 7) | HGF gene fragment 8 (HGF-F8) |
| gHGF6 (SEQ ID NO: 10) | gHGF7 (SEQ ID NO: 7) | HGF gene fragment 6 (HGF-F6) |

The amplified HGF-F2 comprised the sequence ranging from 392 to 2247 of human HGF cDNA prototype (HGF-X1; composed of exons 1 to 4-intron 4-exons 5 to 18) of SEQ ID NO: 2; HGF-F3, the sequence ranging from 392 to 727; HGF-5, the sequence ranging from 2229 to 5471; HGF-F6, the sequence ranging from 5117 to 5471; HGF-F7, the sequence ranging from 3168 to 5471; and HGF-F8, the sequence ranging from 4168 to 5471.

Figure 2:
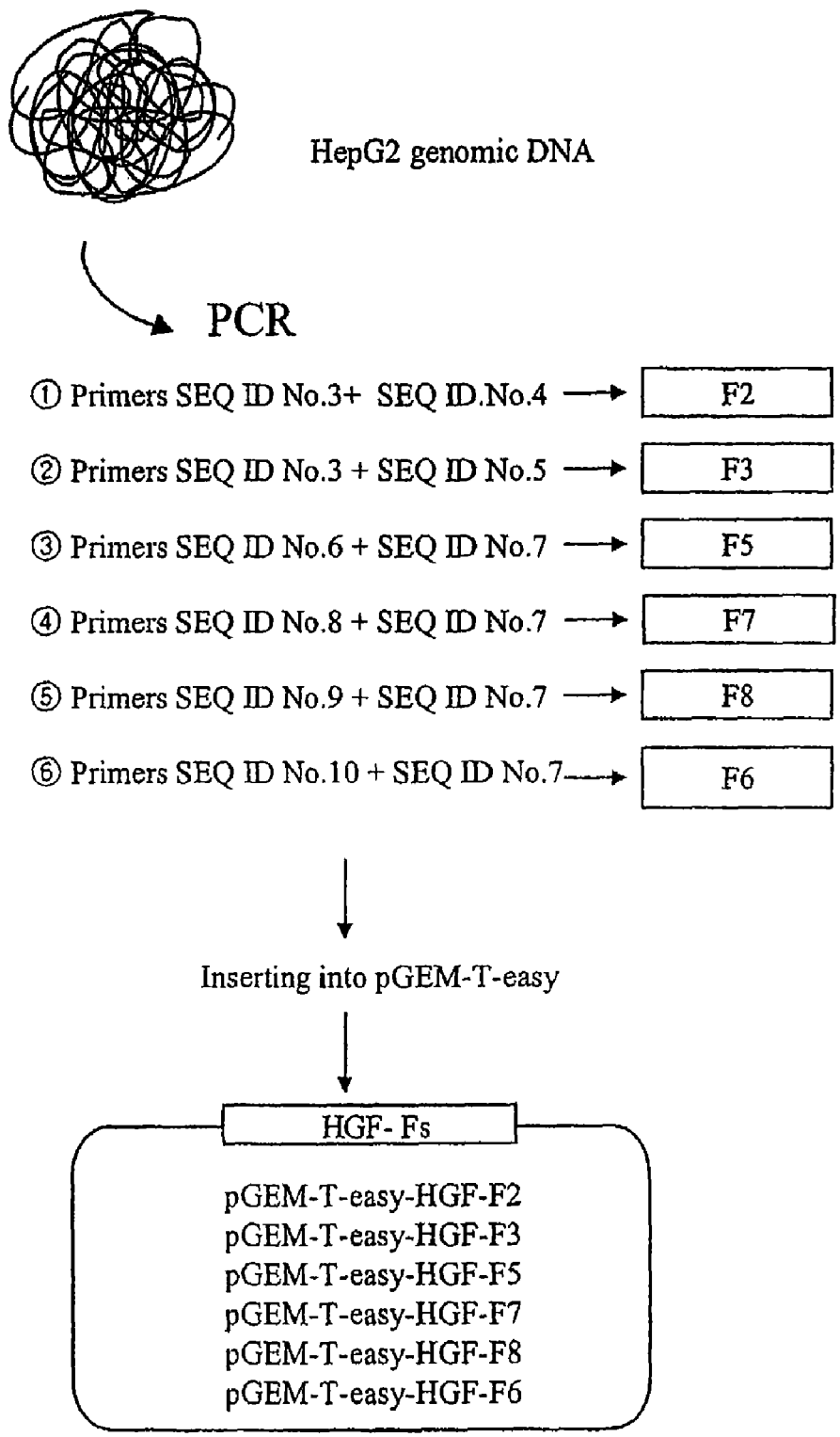
FIG. 2: a process for cloning gene fragments from HepG2 genomic DNA.

The amplified HGF gene fragments were each inserted into the multiple cloning site of pGEM-T easy vector (Promega, Wis., USA) to obtain pGEM-T easy-HGF-F2, pGEM-T easy-HGF-F3, pGEM-T easy-HGF-F5, pGEM-T easy-HGF-F6, pGEM-T easy-HGF-F7 and pGEM-T easy-HGF-F8, respectively (FIG. 2). The nucleotide sequences of the amplified HGF gene fragments were confirmed by a sequence analysis.

(2) Cloning of HGF Gene Fragments Obtained from cDNA

In the PCR amplification, human placenta cDNA (Clontech, Calif., USA) was employed as a template DNA under the same condition as described in Example 1. As primer pairs, the synthetic oligonucleotides of SEQ ID NOs: 11 and 12, and SEQ ID NOs: 13 and 14 were employed to obtain DNA fragments containing HGF-F1 and HGF-F4, respectively. Further, DNA fragments containing cDNAs of HGF gene (cHGF) and deleted HGF gene (dHGF) were amplified by PCR using synthetic oligonucleotides of SEQ ID NOs: 15 and 16 as a primer pair, respectively. dHGF is a HGF gene with deletion of 5 base sequences.

The primers used herein and the amplified gene fragments obtained therefrom are shown in Table 2.

TABLE 2

| 5' primer | 3' primer | Amplified fragment |
|---|---|---|
| gHGF1 (SEQ ID NO: 11) | gHGF2 (SEQ ID NO: 12) | HGF gene fragment 1 (HGF-F1) |
| gHGF8 (SEQ ID NO: 13) | gHGF9 (SEQ ID NO: 14) | HGF gene fragment 4 (HGF-F4) |
| cHGF5 (SEQ ID NO: 15) | cHGF3 (SEQ ID NO: 16) | HGF gene cDNA (cHGF) dHGF gene cDNA (dHGF) |

The amplified HGF-F1 and HGF-F4 comprised the nucleotide sequences ranging from 1 to 402 and from 6533 to 7113 of SEQ ID NO: 2 of human HGF cDNA prototype, respectively. HGF gene cDNA comprised the nucleotide sequence ranging from 1 to 2184 of SEQ ID NO: 1 of human HGF gene, and dHGF gene cDNA has the same sequence as HGF gene cDNA except for the deletion of the sequence ranging from 483 to 495.

Figure 3:
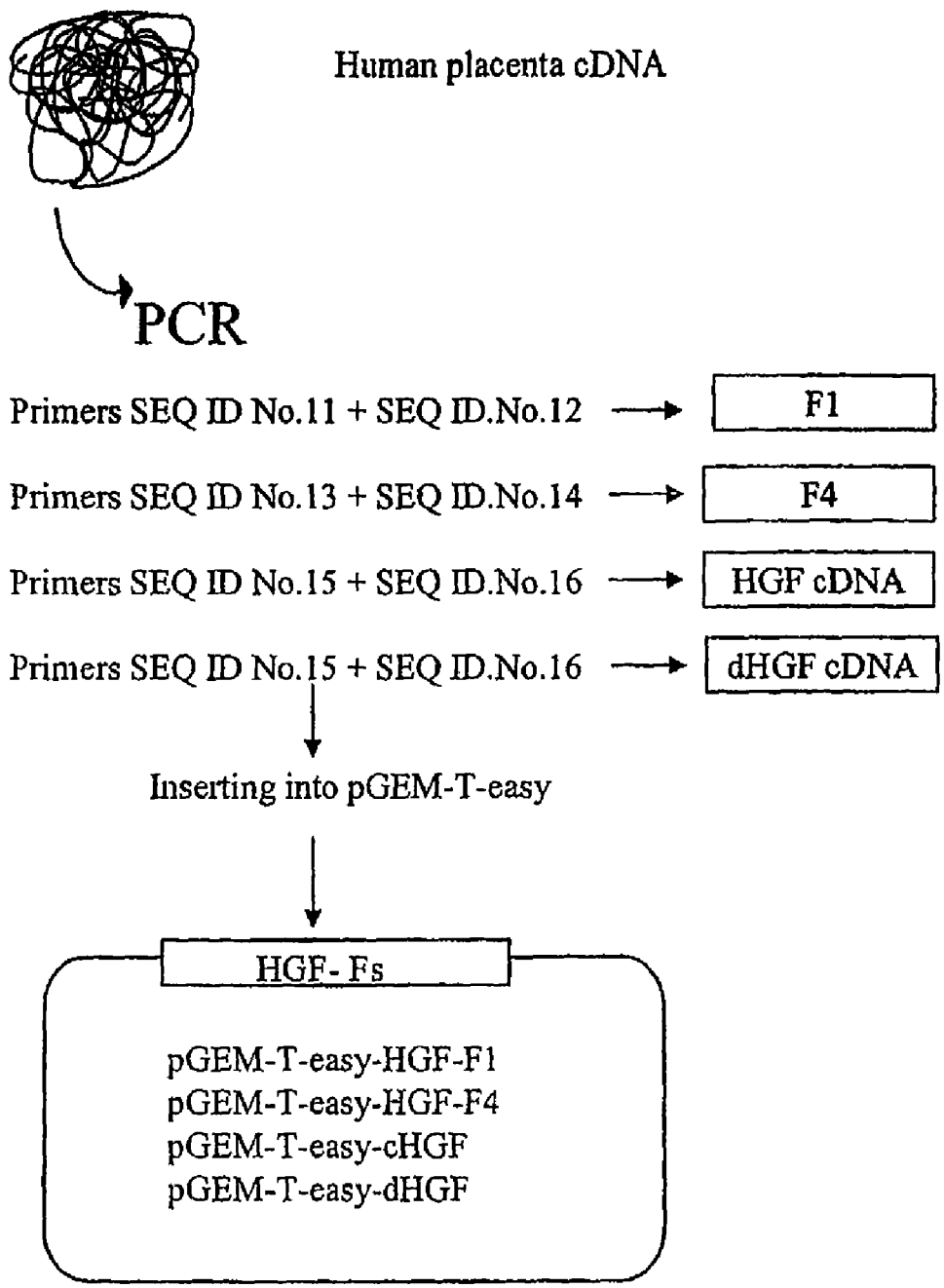
FIG. 3: a process for cloning gene fragments from human placenta cDNA.

The amplified fragments of HGF gene were each inserted into the multiple cloning site of pGEM-T easy vector (Promega, Wis., USA) to obtain pGEM-T easy-HGF-F1, pGEM-T easy-HGF-F4, pGEM-T easy-cHGF and pGEM-T easy-dHGF, respectively (FIG. 3). The nucleotide sequences of the human HGF gene fragments, HGF gene cDNA and dHGF gene cDNA were confirmed by sequence analyses.

(3) Preparation of Hybrid HGF Gene Constructs

Figure 4A:
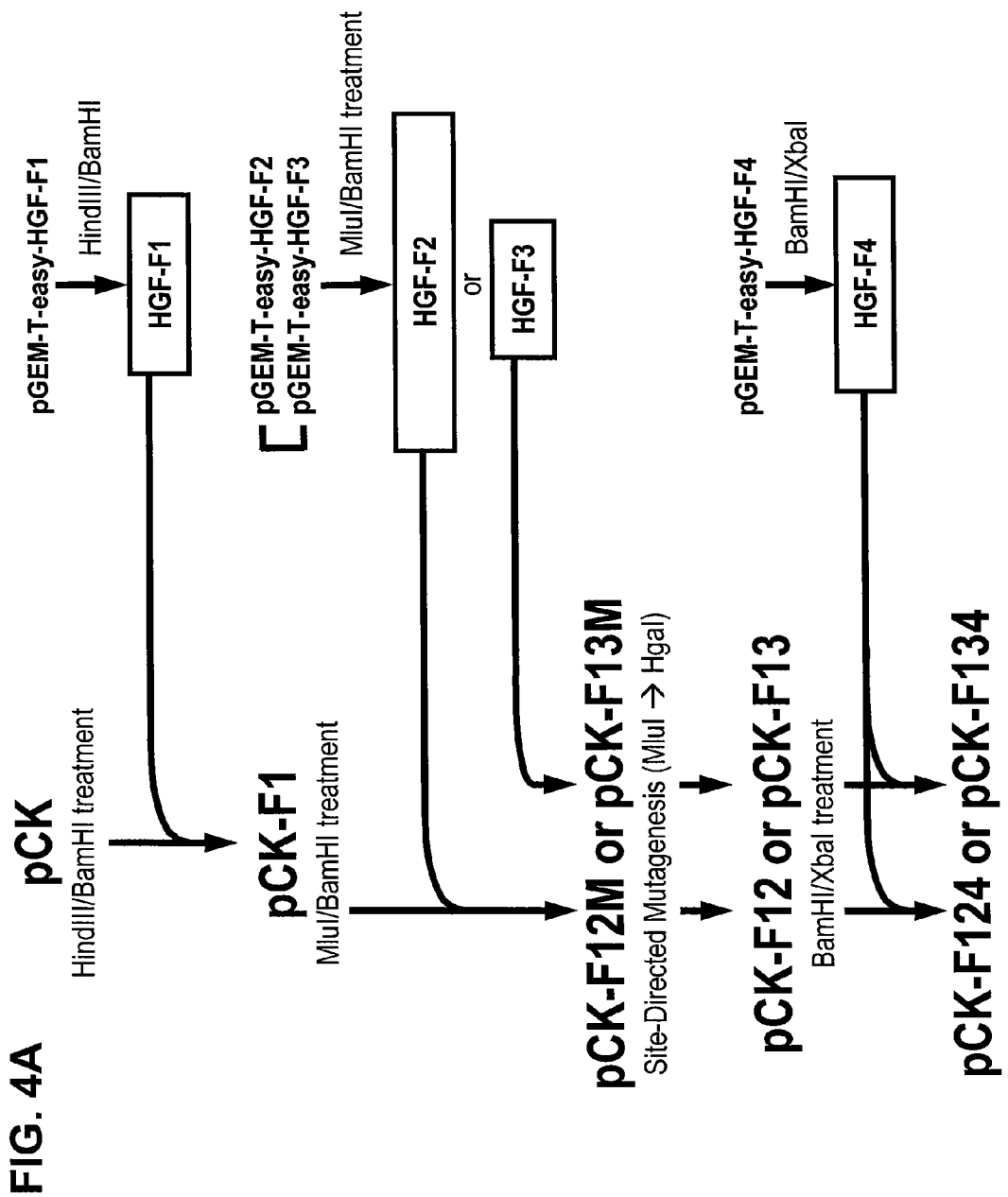
FIGS. 4A and 4B: processes for preparing expression vectors pCK-HGF-X.
Figure 4B:
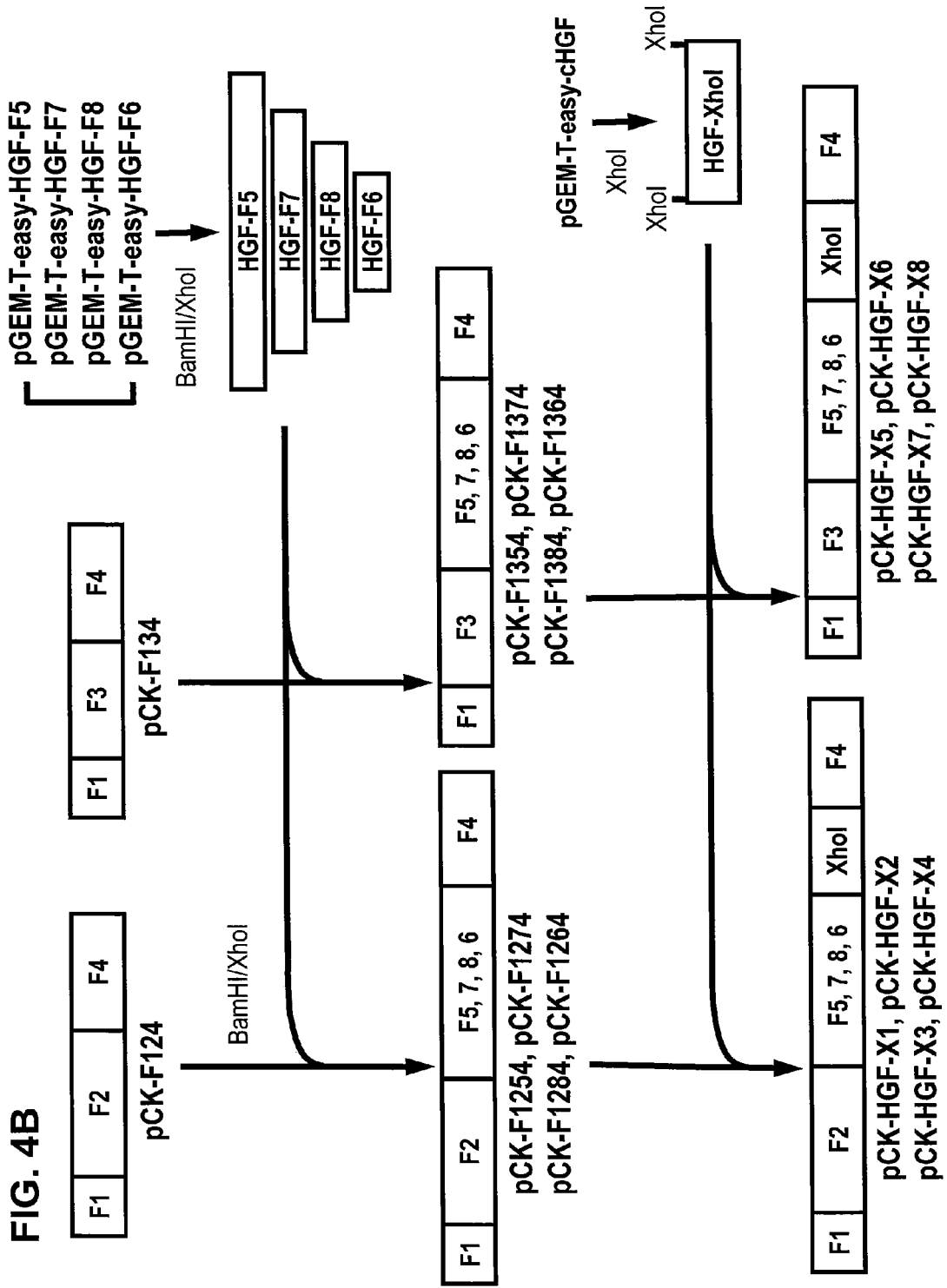

Hybrid HGF gene constructs of genomic DNA and cDNA were prepared by combining the fragments of HGF gene cloned in steps (1) and (2) as follows (FIGS. 4A and 4B).

Plasmid pGEM-T-easy-HGF-F1 was treated with HindIII/BamHI to obtain HGF-F1. Plasmid pCK (see PCT International Publication NO: WO/0040737) was treated with HindIII/BamHI, and HGF-F1 was inserted thereinto to obtain pCK-F1. And then, plasmids pGEM-T-easy-HGF-F2 and pGEM-T-easy-HGF-F3 were treated with MluI/BamHI to obtain HGF-F2 and HGF-F3, respectively. pCK-1 was treated with MluI/BamHI, and then HGF-F2 and HGF-F3 were inserted thereinto to obtain pCK-F12M and pCKF13M. The MluI restriction site of vectors pCK-F12M and pCK-F13M was substituted with an HgaI restriction site by employing a site-directed mutagenesis kit (Stratagene, Calif., USA) to obtain pCK-F12 and pCK-F13, respectively.

Further, plasmid pGEM-T-easy-HGF-F4 was treated with BamHI/XbaI to obtain HGF-F4. pCK-F12 and pCK-F13 were treated with BamHI/XbaI, and HGF-F4 was inserted thereinto to obtain pCK-F124 and pCK-F134, respectively. And then, plasmids pGEM-T-easy-HGF-F5, pGEM-T-easy-HGF-F6, pGEM-T-easy-HGF-F7 and pGEM-T-easy-HGF-F8 were treated with BamHI/XhoI to obtain HGF-F5, HGF-F6, HGF-F7 and HGF-F8, respectively. pCK-F124 and pCK-F134 were treated with BamHI/XhoI, and then HGF-F5, HGF-F6, HGF-F7 and HGF-F8 were inserted thereinto to obtain pCK-F1254 and pCK-F1264, pCK-F1274, pCK-F1284, pCK-F1354, pCK-F 1364, pCK-F 1374 and pCK-F 1384, respectively.

Figure 5:
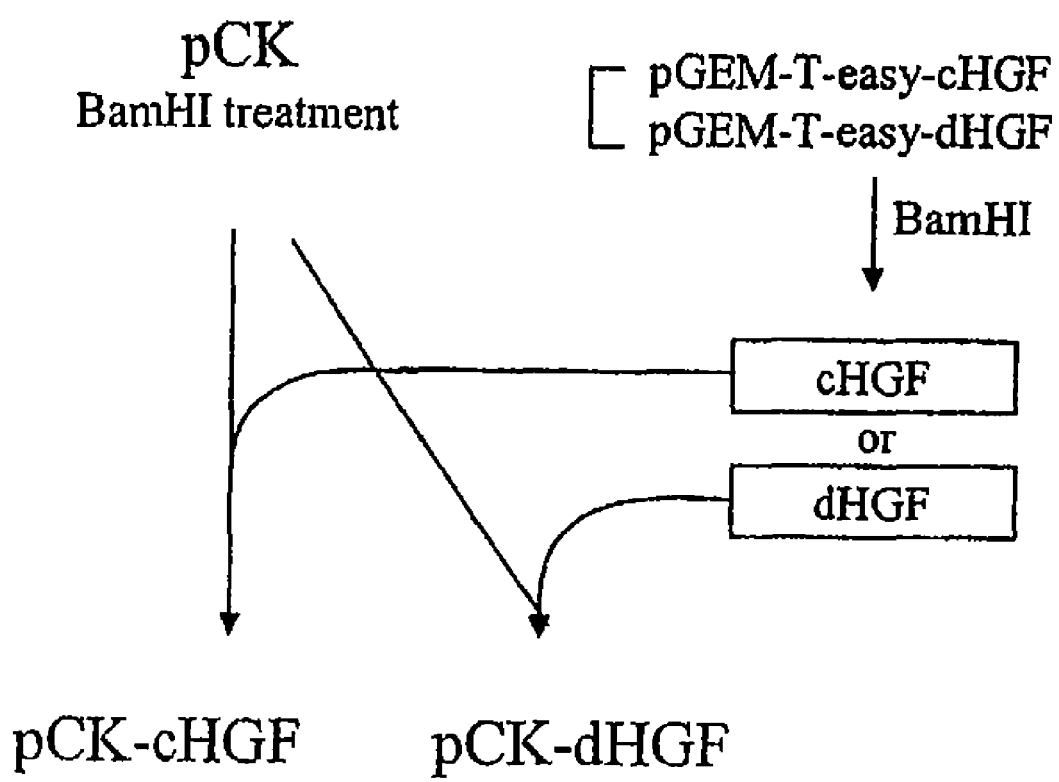
FIG. 5: a process for preparing expression vectors pCK-cHGF and pCK-dHGF.

And then, pGEM-T easy-cHGF was treated with XhoI to obtain cDNA fragment of HGF gene (HGF-XhoI) of about 1100 bp. Then, HGF-XhoI was inserted into pCK-F1254, pCK-F1264, pCK-F1274, pCK-F1284, pCK-F1354, pCK-F1364, pCK-F1374 and pCK-F1384 to obtain pCK-HGF-X1, pCK-HGF-X2, pCK-HGF-X3, pCK-HGF-X4, pCK-HGF-X5, pCK-HGF-X6, pCK-HGF-X7 and pCK-HGF-X8, respectively. On the other hand, pGEM-T easy-cHGF and pGEM-T easy-dHGF were treated with BamHI to obtain HGF gene cDNA and dHGF gene cDNA. Then, HGF gene cDNA and dHGF gene cDNA were inserted into the BamHI restriction site of pCK to obtain pCK-cHGF and pCK-dHGF, respectively (FIG. 5).

(4) Preparation of an Expression Vector Containing a Hybrid HGF Gene Construct

Figure 6:
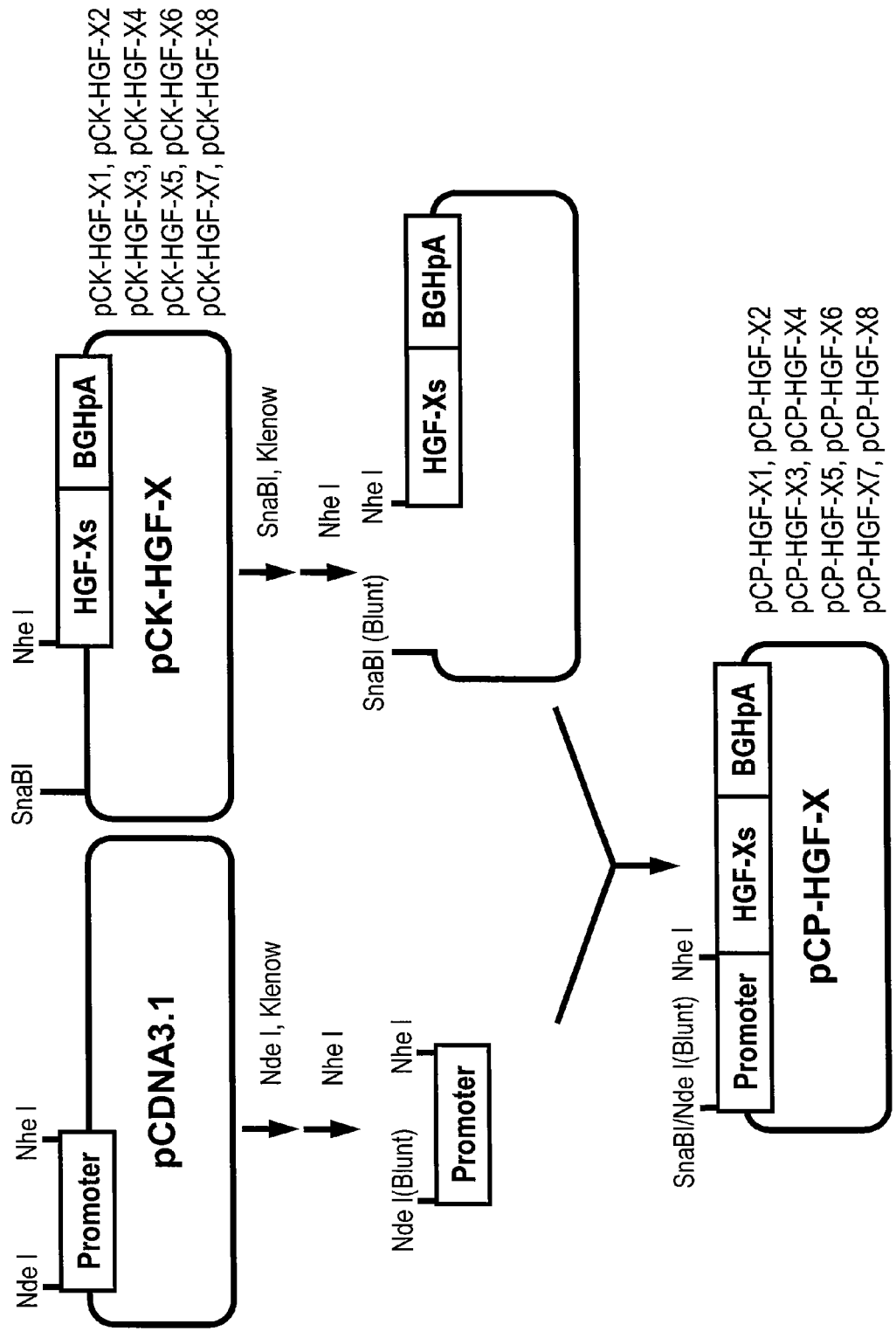
FIG. 6: a process for preparing expression vectors pCP-HGF-X family.

Plasmid pcDNA3.1 (Invitrogen, USA) was digested with NdeI, treated with the Klenow fragment to build blunt ends, and then digested with NheI to obtain a DNA fragment containing human cytomegalovirus promoter. Plasmids pCK-HGF-X1, pCK-HGF-X2, pCK-HGF-X3, pCK-HGF-X4, pCK-HGF-X5, pCK-HGF-X6, pCK-HGF-X7 and pCK-HGF-X8 were digested with SnaBI, treated with the Klenow fragment to make blunt ends and digested with NheI, and then the above DNA fragment containing human cytomegalovirus promoter was inserted thereinto to obtain pCP-HGF-X1, pCP-HGF-X2, pCP-HGF-X3, pCP-HGF-X4, pCP-HGF-X5, pCP-HGF-X6, pCP-HGF-X7 and pCP-HGF-X8, respectively (FIG. 6).

Figure 7:
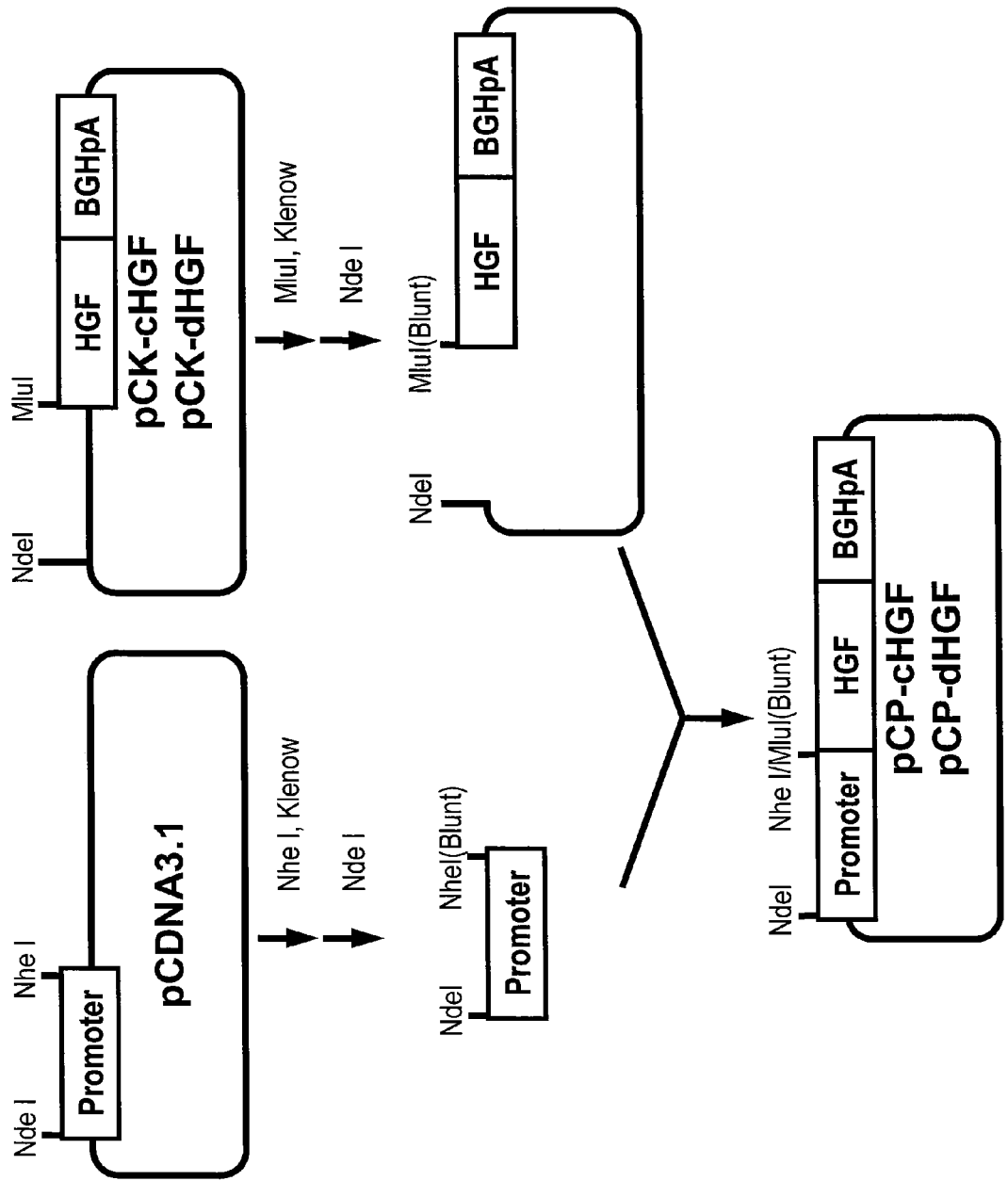
FIG. 7: a process for preparing expression vectors pCP-cHGF and pCP-dHGF.

Plasmid pCDNA3.1 (Invitrogen, USA) was digested with NheI, treated with the Klenow fragment to make blunt ends and digested with NdeI to obtain the DNA fragment containing human cytomegalovirus promoter. pCK-cHGF and pCK-dHGF were digested with MluI, treated with the Klenow fragment to make blunt ends and digested with NdeI, and then the above DNA fragment containing human cytomegalovirus promoter was inserted thereinto to obtain pCP-cHGF and pCP-dHGF, respectively (FIG. 7).

EXAMPLE 2

Examination of the Expression Efficiency of Hybrid HGF Gene Construct and the Coexpression of HGF/dHGF Studies was conducted to examine whether the hybrid HGF gene constructs (HGF-X1 to HGF-X8) obtained in Example 1 can simultaneously express HGF and dHGF and whether there is any difference in the gene expression level between hybrid HGF gene constructs and HGF cDNA.

(1) Gene Expression Efficiency

First, 5 μg of pCP-HGF-X2, pCP-HGF-X3, pCP-HGF-X6, pCP-HGF-X7 and pCP-HGF-X8 were transfected into $5 \times 10^6$ cells of 293 cell (ATCC CRL 1573) together with 0.5 μg of DONAI-LacZ (TAKARA SHUZO, Japan) DNA using FuGENE6 (Gibco BRL, Md., USA), according to the manufacturer's instructions. At this time, 5 μg each of pCP-cHGF and pCP-dHGF were used as controls, and DONAI-LacZ DNA was used to calibrate the infection efficiency. 3 hours after transfection, cells were re-fed with a fresh medium and further cultured for 48 hours. The culture solution thus obtained was divided into two parts. One part of the 293 cell culture solution was subjected to RNA extraction, and the other, to measurement of LacZ activity. The LacZ activity was measured using an activity measuring kit (Stratagene, Calif., USA) according to the manufacturer's instructions.

Figure 8:
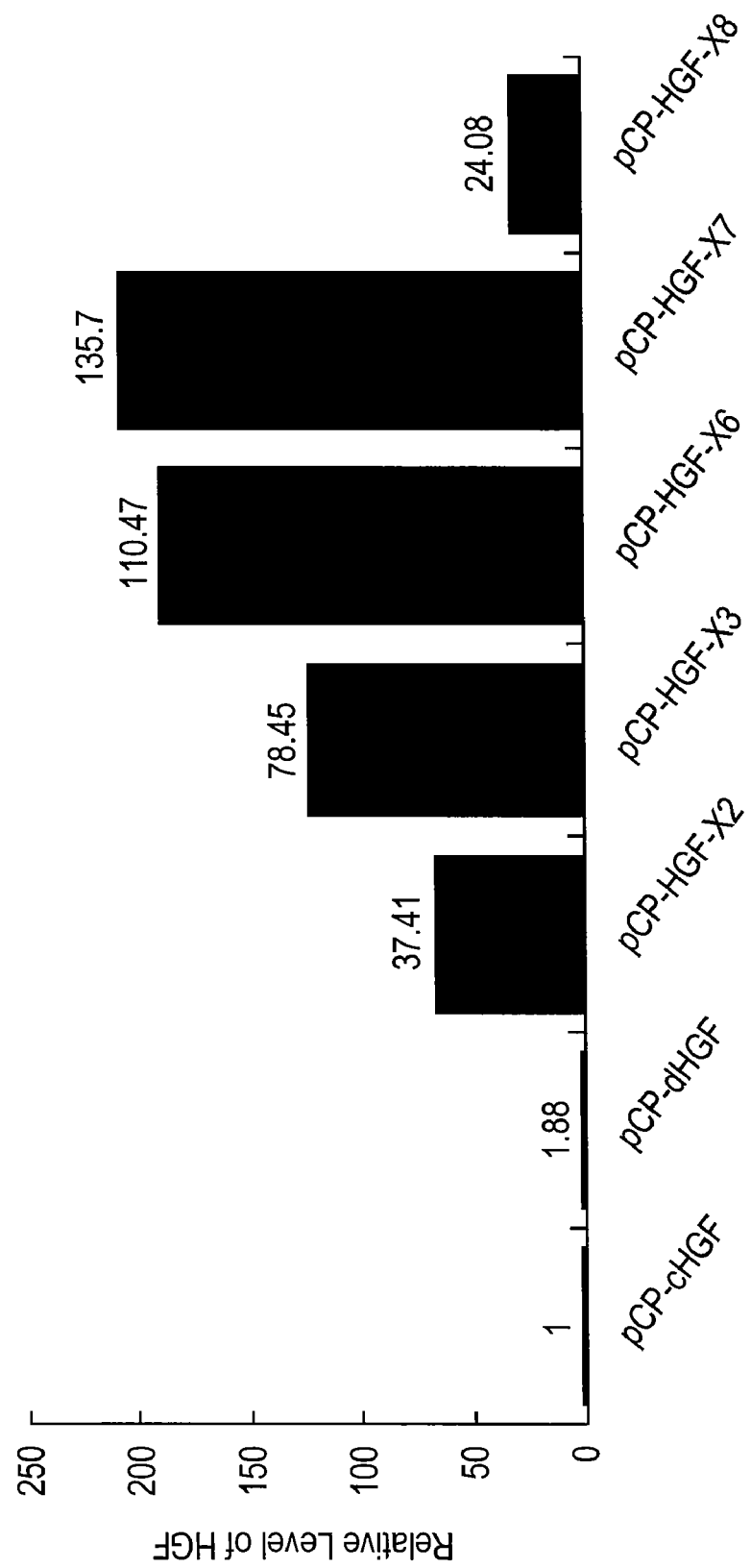
FIG. 8: gene expression levels of pCP-cHGF, pCP-dHGF and pCP-HGF-X.

In order to compare the gene expression levels, the amount of HGF in the cell culture was measured by an enzyme-linked immunosorbent assay kit (ELISA, R&D System, Minn., USA). After calibrating the infection efficiency by the measured LacZ activity, the expression level of HGF-X gene was found to be from 20 to 150-fold higher than those of HGF cDNA and dHGF cDNA (FIG. 8). HGF-X7, in particular, showed the highest gene expression level.

(2) Coexpression of HGF and dHGF

In order to examine coexpression of HGF and dHGF from hybrid HGF gene constructs, total cellular RNAs were extracted from the transfected 293 cells using the Trizol method (Trizol; Gibco BRL, USA) and subjected to RT-PCR to obtain cDNA. Then, using cDNA as a template DNA, PCR amplification was carried out using synthetic oligonucleotides of SEQ ID NOs: 17 and 18 as a primer pair. The PCR amplification mixture was prepared by mixing 1 μl of the template DNA, 1 μl each of the primer (10 pmol/μl), 10 μl of dNTP (10 mM), 3.5 unit of Taq polymerase (TAKARA SHUZO, Japan) and 10 μl of enzyme buffer solution and adjusted to a final volume of 100 μl with distilled water. 30 cycles of PCR amplication was conducted, each cycle consisting of 1 min at 94° C., 1 min at 55° C., and 90 sec at 72° C.

The amplified PCR products corresponded to the boundary region between exons 4 and 5 of HGF gene; HGF gene cDNA of 142 bp and dHGF gene cDNA of 127 bp, respectively. With no splicing, the PCR product of at least 1 kb in length was amplified; and if alternative splicing occurred, HGF gene cDNA of 142 bp and dHGF gene cDNA of 127 bp were simultaneously synthesized and amplified. The amplified PCR products were distinguished by electrophoresis on a 12% polyacrylamide gel.

Figure 9:
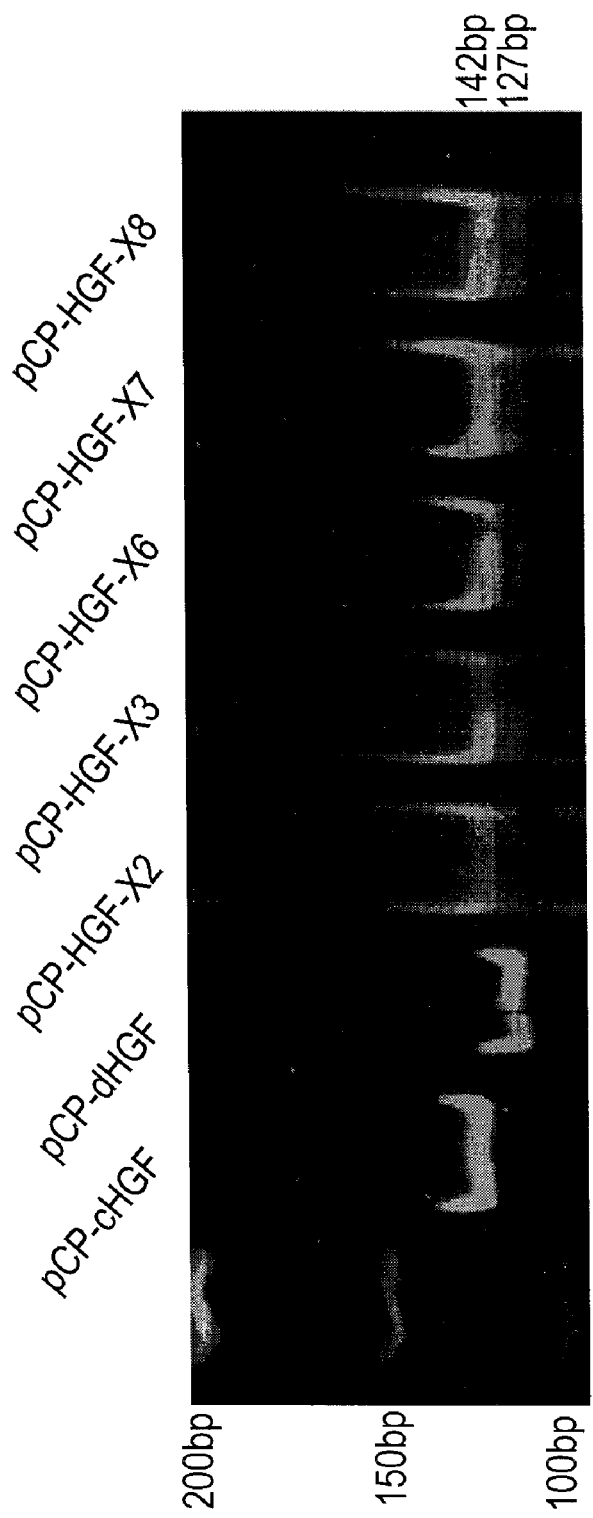
FIG. 9: gene expression patterns of pCP-cHGF, pCP-dHGF and pCP-HGF-X observed by electrophoresis on 12% polyacrylamide gel.

As shown in FIG. 9, while the bands of 142 bp and 127 bp were detected in the lanes loading HGF gene cDNA and dHGF gene cDNA, respectively, both bands of 142 bp and 127 bp were detected in the lanes loading HGF-X. The above results suggest that HGF and dHGF are simultaneously expressed from hybrid HGF-X gene constructs of the present invention.

EXAMPLE 3

Comparison of Expression Levels of HGF-X7, HGF Gene cDNA and dHGF Gene cDNA (in vivo)

100 μg each of pCP-HGF-X7, pCP-cHGF and pCP-dHGF were injected into the enterior tibial muscle of the hind limb of mice with an insulin syringe. After 5 days, the mice were sacrificed and the muscles around the injection spot were removed and smashed in a protein extraction buffer (25 mM Tris-HCl(pH 7.4), 50 mM NaCl, 0.5% Na-deoxycholate, 2% NP-40, 0.2% SDS) to separate total proteins. The amount of the total proteins was measured with a DC protein analysis kit (Bio-Rad Laboratories, California, USA) and the amount of expressed HGF was determined with an ELISA kit (R&D System) according to the manufacturer's instruction.

Figure 10:
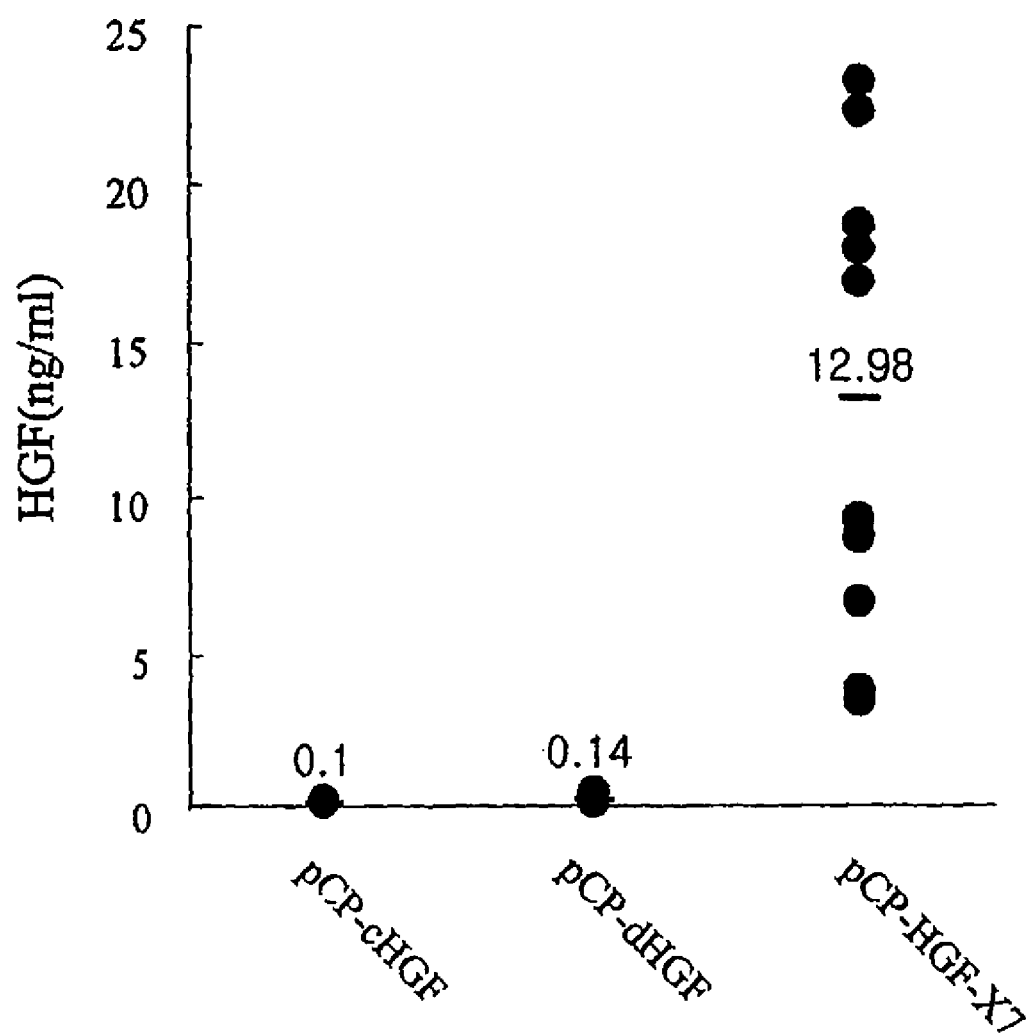
FIG. 10: gene expression levels of pCP-cHGF, pCP-dHGF and pCP-HGF-X7, in vivo.

As can be seen from the result shown in FIG. 10, the amount of HGF expressed from HGF-X7 is 250-fold higher than that from HGF gene cDNA or dHGF gene cDNA.

Together with the result of the experiment of Example 2 (in vivo), this result demonstrates that the expression efficiency of HGF-X gene is much superior to those of HGF gene cDNA or dHGF gene cDNA.

EXAMPLE 4

Gene Therapy Employing HGF-X7 in a Rabbit Ischemic Hind Limb Model

In order to examine whether HGF-X7 gene is effective in the treatment of ischemic hind limb disease, gene therapy was carried out on a rabbit ischemic hind limb model as follows.

A rabbit ischemic hind limb model, which is a standard animal model for the ischemic limb disease, was prepared by the method described by Takeshita et al., *Journal of Clinical*

*Investigation* 93:662 (1994). At the day before operation (day 0), each of 30 white rabbits from New Zealand (male, from 3.8 to 4.2 kg) was intramuscularly injected with 5 mg/kg of xylazine and, then, anesthetized by an intramuscular injection of 50 mg/kg of ketamine. Subsequently, the left femoral region of the rabbit was incised and all branches of the femoral artery were separated and tied. The region from the proximal part to the branching point of the saphenous and popliteal arteries was incised to prepare the model. After the operation, 15 mg/kg/day of cefazolin was injected intramuscularly for 5 days and 0.3 mg/day of morphin, for 10 days. 10 days after the operation (day 10), angiography was carried out for the left hind limb where the ischemia was induced, and the degree of arteriogenesis was recorded as a basal level. The rabbits were randomly divided into two groups and injected at four sites in the femoral muscle with 500 μg of plasmid pCP-HGF-X7 (experimental group) or 500 μg of plasmid pCP (control), respectively. 40 days after the operation (day 40), angiography was carried out again for the left hind limb and the degree of arteriogenesis at the arteriole level was determined and compared to that of day 10.

Figure 11:
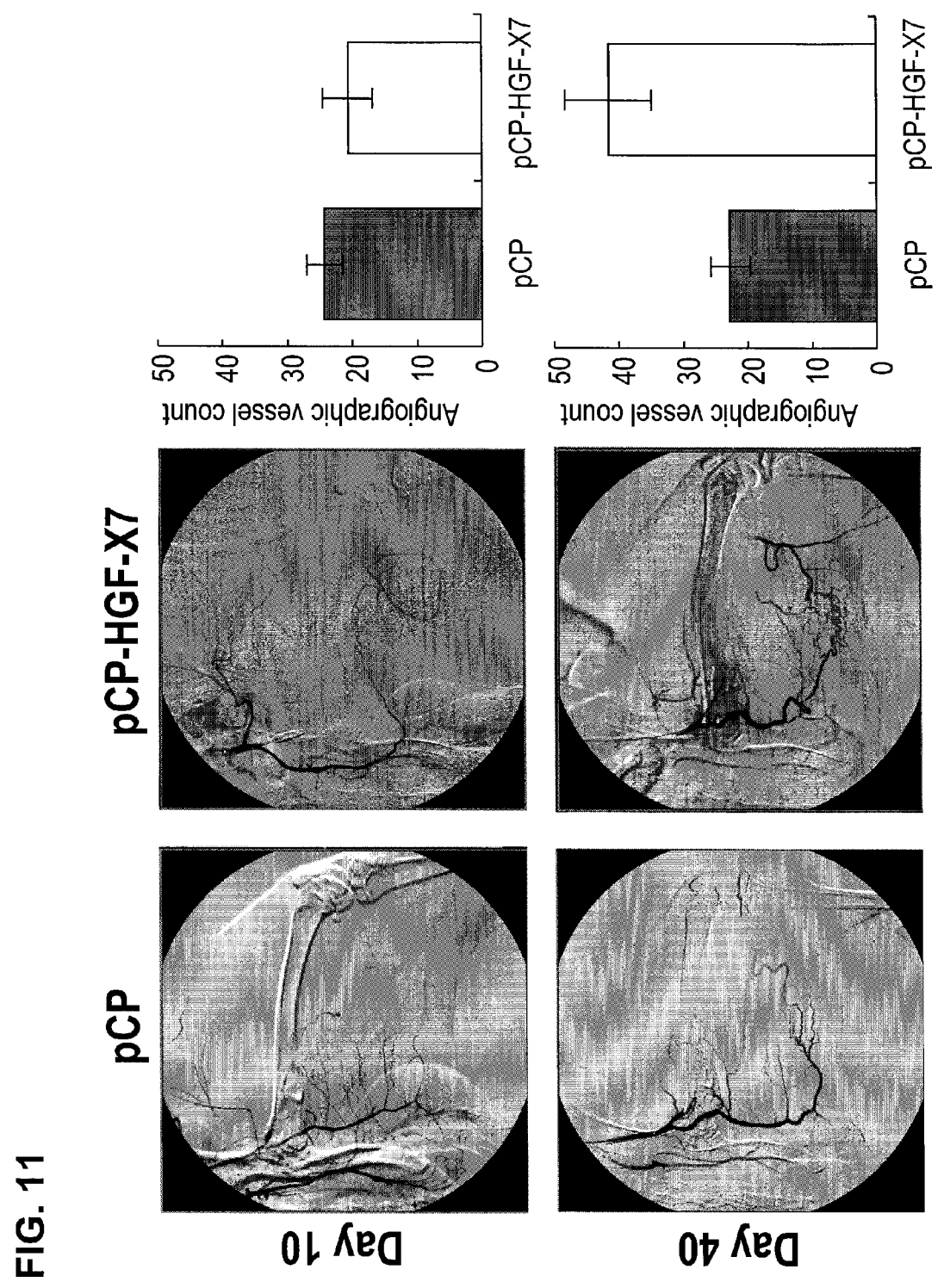

As can be seen from the result in FIG. 11, the degree of angiogenesis was significantly enhanced in the experimental group administered with pCP-HGF-X7 as compared with the pCP-administered control group.

This result demonstrates that HGF-X7 gene can be effectively used in the gene therapy of an ischemic disease.

While the invention has been described with respect to the above specific embodiments, it should be recognized that various modifications and changes may be made to the invention by those skilled in the art which also fall within the scope of the invention as defined by the appended claims.

What is claimed:

1. A method of increasing angiogenesis in a tissue of a subject comprising administering to the tissue of said subject a hybrid Hepatocyte Growth Factor (HGF) construct comprising
   (a) a first cDNA which has the same sequence as exons 1-4 of the human HGF gene wherein said exons 1-4 are arranged in sequential order without an intron therebetween, or degenerates thereof which do not alter the amino acid sequence encoded by said first cDNA,
   (b) a polynucleotide that has the same sequence as intron 4 of a HGF gene or a fragment thereof, and
   (c) a second cDNA which has the same sequence as exons 5-18 of the human HGF gene wherein said exons 5-18 are arranged in sequential order without an intron therebetween, or degenerates thereof which do not alter the amino acid sequence encoded by said second cDNA;
   wherein (b) is located between (a) and (c); and the HGF construct simultaneously encodes two heterotypes of human HGF, wherein said administration results in increased angiogenesis in said tissue.

2. The method of claim 1, wherein the polynucleotide of (b) has the same sequence as the full intron 4 of the human HGF gene.

3. The method of claim 2, wherein said hybrid HGF construct comprises a nucleotide sequence comprising SEQ ID NO: 2.

4. The method of claim 1, wherein the polynucleotide of (b) has the same sequence as a fragment of intron 4 of the human HGF gene.

5. The method of claim 4, wherein said hybrid HGF construct comprises SEQ ID NO: 19.

6. The method of claim 4, wherein said hybrid HGF construct comprises SEQ ID NO: 20.

7. The method of claim 4, wherein said hybrid HGF construct comprises SEQ ID NO: 21.

8. The method of claim 1, wherein said hybrid HGF construct is a vector.

9. The method of claim 8, wherein said vector further comprises one or more sequences for regulating expression, a self-replication sequence, or a secretory signal.

10. The method of claim 8, wherein said vector is selected from the group consisting of: pCK-HGF-X2, pCK-HGF-X3, pCK-HGF-X6, pCK-HGF-X7, pCK-HGF-X8, pCP-HGF-X2, pCP-HGF-X3, pCP-HGF-X6, pCP-HGF-X7 and pCP-HGF-X8.

11. The method of claim 1, wherein said hybrid HGF construct is administered intramuscularly to said tissue.

12. The method of claim 1, wherein said tissue is an ischemic limb.

13. A method of increasing angiogenesis in a tissue of a subject comprising administering to the tissue of said subject a hybrid Hepatocyte Growth Factor (HGF) construct comprising a polynucleotide having a nucleotide sequence not less than 90% identical to SEQ ID NO: 2, wherein the polynucleotide having said nucleotide sequence simultaneously encodes two heterotypes of human HGF, wherein said administration results in increased angiogenesis in said tissue.

14. The method of claim 13, wherein said nucleotide sequence is not less than 95% identical to SEQ ID NO: 2.

15. A method of increasing angiogenesis in a tissue of a subject comprising administering to the tissue of said subject a hybrid Hepatocyte Growth Factor (HGF) construct comprising a polynucleotide having a nucleotide sequence not less than 90% identical to SEQ ID NO: 19, wherein the polynucleotide having said nucleotide sequence simultaneously encodes two heterotypes of human HGF, wherein said administration results in increased angiogenesis in said tissue.

16. The method of claim 15, wherein said nucleotide sequence is not less than 95% identical to SEQ ID NO: 19.

17. A method of increasing angiogenesis in a tissue of a subject comprising administering to the tissue of said subject a hybrid Hepatocyte Growth Factor (HGF) construct comprising a polynucleotide having a nucleotide sequence not less than 90% identical to SEQ ID NO: 20, wherein the polynucleotide having said nucleotide sequence simultaneously encodes two heterotypes of human HGF, wherein said administration results in increased angiogenesis in said tissue.

18. The method of claim 17, wherein said nucleotide sequence is not less than 95% identical to SEQ ID NO: 20.

19. A method of increasing angiogenesis in a tissue of a subject comprising administering to the tissue of said subject a hybrid Hepatocyte Growth Factor (HGF) construct comprising a polynucleotide having a nucleotide sequence not less than 90% identical to SEQ ID NO: 21, wherein the polynucleotide having said nucleotide sequence simultaneously encodes two heterotypes of human HGF, wherein said administration results in increased angiogenesis in said tissue.

20. The method of claim 19, wherein said nucleotide sequence is not less than 95% identical to SEQ ID NO: 21.

* * * * *

SEQUENCE LISTING

<160> NUMBER OF SEQ ID NOS: 21

<210> SEQ ID NO 1
<211> LENGTH: 2187
<212> TYPE: DNA
<213> ORGANISM: Homo sapiens

<400> SEQUENCE: 1

```
atgtgggtga ccaaactcct gccagccctg ctgctgcagc atgtcctcct gcatctcctc      60
ctgctcccca tcgccatccc ctatgcagag ggacaaagga aagaagaaa tacaattcat     120 gaattcaaaa aatcagcaaa gactaccta atcaaaatag atccagcact gaagataaaa      180
accaaaaaag tgaatactgc agaccaatgt gctaatagat gtactaggaa taaaggactt     240
ccattcactt gcaaggcttt tgtttttgat aaagcaagaa aacaatgcct ctggttcccc     300
ttcaatagca tgtcaagtgg agtgaaaaaa gaatttggcc atgaatttga cctctatgaa     360
aacaaagact acattagaaa ctgcatcatt ggtaaaggac gcagctacaa gggaacagta     420
tctatcacta agagtggcat caaatgtcag ccctggagtt ccatgatacc acacgaacac     480 agcttttgc cttcgagcta tcggggtaaa gacctacagg aaaactactg tcgaaatcct     540
cgaggggaag aagggggacc ctggtgtttc acaagcaatc cagaggtacg ctacgaagtc     600
tgtgacattc ctcagtgttc agaagttgaa tgcatgacct gcaatgggga gagttatcga     660
ggtctcatgg atcatacaga atcaggcaag atttgtcagc gctgggatca tcagacacca     720
caccggcaca aattcttgcc tgaaagatat cccgacaagg gctttgatga taattattgc     780
cgcaatcccg atggccagcc gaggccatgg tgctatactc ttgaccctca cacccgctgg     840
gagtactgtg caattaaaac atgcgctgac aatactatga atgacactga tgttcctttg     900
gaaacaactg aatgcatcca aggtcaagga gaaggctaca ggggcactgt caataccatt     960
tggaatggaa ttccatgtca gcgttgggat tctcagtatc ctcacgagca tgacatgact    1020
cctgaaaatt tcaagtgcaa ggacctacga gaaaattact gccgaaatcc agatgggtct    1080
gaatcaccct ggtgttttac cactgatcca aacatccgag ttggctactg ctcccaaatt    1140
ccaaactgtg atatgtcaca tggacaagat tgttatcgtg ggaatggcaa aaattatatg    1200
ggcaacttat cccaaacaag atctggacta acatgttcaa tgtgggacaa gaacatggaa    1260
gacttacatc gtcatatctt ctgggaacca gatgcaagta agctgaatga gaattactgc    1320
cgaaatccag atgatgatgc tcatggaccc tggtgctaca cgggaaatcc actcattcct    1380
```

-continued

```
tgggattatt gccctatttc tcgttgtgaa ggtgatacca cacctacaat agtcaattta    1440
gaccatcccg taatatcttg tgccaaaacg aaacaattgc gagttgtaaa tgggattcca    1500
acacgaacaa acataggatg gatggttagt ttgagataca gaaataaaca tatctgcgga    1560
ggatcattga taaaggagag ttgggttctt actgcacgac agtgtttccc ttctcgagac    1620
ttgaaagatt atgaagcttg gcttggaatt catgatgtcc acggaagagg agatgagaaa    1680
tgcaaacagg ttctcaatgt ttcccagctg gtatatggcc ctgaaggatc agatctggtt    1740
ttaatgaagc ttgccaggcc tgctgtcctg gatgattttg ttagtacgat tgatttacct    1800
aattatggat gcacaattcc tgaaaagacc agttgcagtg tttatggctg gggctacact    1860
ggattgatca actatgatgg cctattacga gtggcacatc tctatataat gggaaatgag    1920
aaatgcagcc agcatcatcg agggaaggtg actctgaatg agtctgaaat atgtgctggg    1980
gctgaaaaga ttggatcagg accatgtgag ggggattatg gtggcccact tgtttgtgag    2040
caacataaaa tgagaatggt tcttggtgtc attgttcctg gtcgtggatg tgccattcca    2100
aatcgtcctg gtattttgt ccgagtagca tattatgcaa aatggataca caaaattatt    2160
ttaacatata aggtaccaca gtcatag                                        2187

<210> SEQ ID NO 2
<211> LENGTH: 7113
<212> TYPE: DNA
<213> ORGANISM: Homo sapiens

<400> SEQUENCE: 2
atgtgggtga ccaaactcct gccagccctg ctgctgcagc atgtcctcct gcatctcctc      60
ctgctcccca tcgccatccc ctatgcagag ggacaaagga aagaagaaa tacaattcat     120 gaattcaaaa aatcagcaaa gactacccta atcaaaatag atccagcact gaagataaaa     180
accaaaaaag tgaatactgc agaccaatgt gctaatagat gtactaggaa taaaggactt     240
ccattcactt gcaaggcttt tgttttttgat aaagcaagaa acaatgcct ctggttcccc     300 ttcaatagca tgtcaagtgg agtgaaaaaa gaatttggcc atgaatttga cctctatgaa     360
aacaaagact acattagaaa ctgcatcatt ggtaaaggac gcagctacaa gggaacagta     420
tctatcacta gagtggcat caaatgtcag ccctggagtt ccatgatacc acacgaacac     480
aggtaagaac agtatgaaga aaagagatga agcctctgtc tttttacat gttaacagtc     540 tcatattagt ccttcagaat aattctacaa tcctaaaata acttagccaa cttgctgaat     600
tgtattacgg caaggtttat atgaattcat gactgatatt tagcaaatga ttaattaata     660
tgttaataaa atgtagccaa acaatatct taccttaatg cctcaatttg tagatctcgg     720
tatttgtgaa ataataacgt aaacttcgtt taaaaggatt cttcttcctg tctttgagaa     780
agtacggcac tgtgcagggg gagaggttga ttgtgaaaaa tcagaggtag atgagaatct     840
tactgagggc tgagggttct ttaaccttgg tggatctcaa cattggttgc acattaaaat     900
cacctgctgc aagcccttga cgaatcttac ttagaagatg acaacacaga acaattaaat     960
cagaatctct ggggagaata gggcaccagt attttttgag ctcccaccat gattccaaag    1020
tgcagccaaa tttgagaacc actgctaaaa gctcaagctt cagattgacc agcttttcca    1080
tctcacctat cgcctaaaga ccaaattgga taaatgtgtt cattacgaca gatgggtact    1140
atttaaagat gagtaaacac aatatactta ggctcgtcag actgagagtt ttaatcatca    1200
ctgaggaaaa acatagatat ctaatactga ctggagtatt agtcaaggct tatttcacac    1260 acaatttttat cagaaaccaa agtagtttaa aacagctctc cccttattag taatgcattg    1320
```

```
gagggtttac tttaccatgt accttgctga gcactgtacc ttgttaatct catttacttg    1380
taatgagaac cacacagcgg gtagtttat tggttctatt ttacctacat gacaaaactg    1440
aagcataaaa acacttagta agttttcagt gtcatgcaca actaggaagt gacatggcca    1500
gaatataagc ccagtcacca tcactctata acctgcgctt ttaacaactt cagggcatga    1560
cacatttggc cggtcagtag aacccatgct gtgatttgtt tttgcagtgg tggtgatgac    1620
tgccttgttg aatccacttt ttattctatt ccattttggg gacacaattc tgcaagatga    1680
ttcttcatta ggaaacagag atgagttatt gaccaacaca gaaagaaaaa gagtttgttg    1740
ctccacactg ggattaaacc tatgatcttg gcctaattaa cactagctag taagtgtcca    1800
agctgatcat ctctacaaca tttcaataac agaaaacaac aattttcaaa attagttact    1860
tacaattatg tagaaatgcc tctaaaacac agtattttcc ttatattaca aaaacaaaaa    1920
ttataattgg ttttgtcctc ttttgagagt ttgcatggtg ttactccctg catagtgaag    1980
aaaacatttt atttaagtag atggatctaa gttttcatg aacaaggaa tgacatttga    2040 aatcaatcct accctagtcc aggagaatgc attagattaa cctagtagag gtcttatttc    2100
accctgagtt ttctatgatc gtgattctct gctggaggag taattgtgaa atagatctct    2160
ctgggaactg gcttcctagt ccaatcagct cttttaccaa tgaacacttc cttgtgatat    2220
agatgtttat ggccgagagg atccagtata ttaataaaat ccctttttgt attcaatgag    2280
ggaaacacat aattttcatc aattagcagc ttattggaat atctgcatga tggtttaaca    2340
cttttaagtg ttgactaaag attaattta cagaaaatag aaaagaaat atgtttctgt    2400 ctggaggaat gatttattgt tgaccctaa attgaaatat tttactagtg cttaatgga    2460 aagatgatga aagatgatga aattaatgta gaagcttaac tagaaaatca ggtgacctga    2520
tatctacatc tgtatccttc attggccacc cagcattcat taatgaatca gatgatggaa    2580
tagatcaagt ttcctaggaa cacagtgaat attaaaagaa aacaaaggga gcctagcacc    2640
tagaagacct agtttatatt tcaaagtata tttggatgta acccaatttt aaacatttcc    2700
tcacttgtct ctcttaaagc cttgccaaca gcaaggacag agaaccaaaa atagtgtata    2760
tatgaataaa tgcttattac agaatctgct gactggcaca tgctttgtgt gtaatgggtt    2820
ctcataaaca cttgttgaat gaacacacat aagtgaaaga gcatggctag gcttcatccc    2880
ttggtcaaat atgggtgct aaagaaaagc aggggaaata cattgggaca ctaacaaaaa    2940
aaaacagtta atttaggtaa aagataaaat acaccacaga atgaagaaaa gagatgaccc    3000
agactgctct ttaaccttca tgtcctagag aggttttga tatgaattgc attcagaatt    3060
gtggaaagga gcccatcttt tctcttcatt ttgattttat taactccaat gggggaattt    3120
tattcgtgtt ttggccatat ctactttga tttctacatt attctctctt cctttctacc    3180
tgtatttgtc ctaataaatt gttgacttat taattcacta cttcctcaca gctttttttt    3240
ggctttacaa atccactgga aaggtatatg ggtgtatcac tttgtgtatt tcggtgtgca    3300
tgtgtagagg ggacaaaaat cctctctcaa actataaata ttgagtattt gtgtattgaa    3360
catttgctat aactactagg tttcttaaat aatcttaata tataaaatga tatagaaaaa    3420
gggaaattat agttcgtatt attcatctaa gtgaagagat taaacccag ggagtaaata    3480 aattgtctaa ggactaaggt tgtatactat ttaggtgata gatatggggc aaccgtatgg    3540
gttttatgat taacaaataa acttctcacc actctaccat atcaacttt ccataaaaga    3600 gagctatagt attctttgct taaataaatt tgattagtgc atgacttctt gaaaacatat    3660
```

```
aaagcaaaag tcacatttga ttctatcaga aaagtgagta agccatggcc caaacaaaag   3720
atgcattaaa atattctgga atgatggagc taaaagtaag aaaaatgact ttttaaaaaa   3780
gtttactgtt aggaattgtg aaattatgct gaattttagt tgcattataa ttttttgtcag  3840 tcatacggtc tgacaacctg tcttatttct atttccccat atgaggaatg ctagttaagt   3900
atggatatta actattacta cttagatgca ttgaagttgc ataatatgga taatacttca   3960
ctggttccct gaaaatgttt agttagtaat aagtctctta cactatttgt tttgtccaat   4020
aatttatatt ttctgaagac ttaactctag aatacactca tgtcaaaatg aaagaatttc   4080
attgcaaaat attgcttggt acatgacgca tacctgtatt tgttttgtgt cacaacatga   4140
aaaatgatgg tttattagaa gtttcattgg gtaggaaaca catttgaatg gtatttacta   4200
agatactaaa atccttggac ttcactctaa ttttagtgcc atttagaact caaggtctca   4260
gtaaaagtag aaataaagcc tgttaacaaa acacaagctg aatattaaaa atgtaactgg   4320 atttttcaaag aaatgtttac tggtattacc tgtagatgta tattctttat tatgatcttt  4380
tgtgtaaagt ctggcagaca aatgcaatat ctaattgttg agtccaatat cacaagcagt   4440
acaaaagtat aaaaaagact tggccttttc taatgtgtta aaatacttta tgctggtaat   4500
aacactaaga gtagggcact agaaatttta agtgaagata atgtgttgca gttactgcac   4560
tcaatggctt actattataa accaaaactg ggatcactaa gctccagtca gtcaaaatga   4620
tcaaaattat tgaagagaat aagcaattct gttctttatt aggacacagt agatacagac   4680
tacaaagtgg agtgtgctta ataagaggta gcatttgtta agtgtcaatt actctattat   4740
cccttggagc ttctcaaaat aaccatataa ggtgtaagat gttaaaggtt atggttacac   4800
tcagtgcaca ggtaagctaa taggctgaga gaagctaaat tacttactgg ggtctcacag   4860
taagaaagtg agctgaagtt tcagcccaga tttaactgga ttctgggctc tttattcatg   4920
ttacttcatg aatctgtttc tcaattgtgc agaaaaaagg gggctattta taagaaaagc   4980
aataaacaaa caagtaatga tctcaaataa gtaatgcaag aaaatagtgag atttcaaaat   5040 cagtggcagc gatttctcag ttctgtccta agtggccttg ctcaatcacc tgctatcttt   5100
tagtggagct ttgaaattat gtttcagaca acttcgattc agttctagaa tgtttgactc   5160
agcaaattca caggctcatc tttctaactt gatggtgaat atggaaattc agctaaatgg   5220
atgttaataa aattcaaacg ttttaaggac agatgaaaat gacagaattt taaggtaaaa   5280
tatatgaagg aatataagat aaaggatttt tctaccttca gcaaaaacat acccactaat   5340
tagtaaaatt aataggcaaa aaaaagttgc atgctcttat actgtaatga ttatcatttt   5400
aaaactagct ttttgccttc gagctatcgg ggtaaagacc tacaggaaaa ctactgtcga   5460
aatcctcgag gggaagaagg gggaccctgg tgtttcacaa gcaatccaga ggtacgctac   5520
gaagtctgtg acattcctca gtgttcagaa gttgaatgca tgacctgcaa tggggagagt   5580
tatcgaggtc tcatggatca tacagaatca ggcaagattt gtcagcgctg ggatcatcag   5640
acaccacacc ggcacaaatt cttgcctgaa agatatcccg acaagggctt tgatgataat   5700
tattgccgca atcccgatgg ccagccgagg ccatggtgct atactcttga ccctcacacc   5760
cgctgggagt actgtgcaat taaaacatgc gctgacaata ctatgaatga cactgatgtt   5820
cctttggaaa caactgaatg catccaaggt caaggagaag gctacagggg cactgtcaat   5880
accatttgga atggaattcc atgtcagcgt tgggattctc agtatcctca cgagcatgac   5940
atgactcctg aaaatttcaa gtgcaaggac ctacgagaaa attactgccg aaatccagat   6000
gggtctgaat cacccggtgg tttttaccact gatccaaaca tccgagttgg ctactgctcc   6060
```

-continued

```
caaattccaa actgtgatat gtcacatgga caagattgtt atcgtgggaa tggcaaaaat      6120
tatatgggca acttatccca acaagatct ggactaacat gttcaatgtg ggacaagaac       6180
atggaagact tacatcgtca tatcttctgg gaaccagatg caagtaagct gaatgagaat      6240
tactgccgaa atccagatga tgatgctcat ggaccctggt gctacacggg aaatccactc     6300
attccttggg attattgccc tatttctcgt tgtgaaggtg ataccacacc tacaatagtc     6360
aatttagacc atcccgtaat atcttgtgcc aaaacgaaac aattgcgagt tgtaaatggg     6420
attccaacac gaacaaacat aggatggatg gttagtttga gatacagaaa taaacatatc     6480
tgcggaggat cattgataaa ggagagttgg gttcttactg cacgacagtg tttcccttct     6540
cgagacttga aagattatga agcttggctt ggaattcatg atgtccacgg aagaggagat      6600
gagaaatgca aacaggttct caatgtttcc cagctggtat atggccctga aggatcagat     6660
ctggttttaa tgaagcttgc caggcctgct gtcctggatg attttgttag tacgattgat      6720
ttacctaatt atggatgcac aattcctgaa aagaccagtt gcagtgttta tggctggggc     6780
tacactggat tgatcaacta tgatggccta ttacgagtgg cacatctcta tataatggga      6840
aatgagaaat gcagccagca tcatcgaggg aaggtgactc tgaatgagtc tgaaatatgt     6900
gctggggctg aaaagattgg atcaggacca tgtgaggggg attatggtgg cccacttgtt     6960
tgtgagcaac ataaaatgag aatggttctt ggtgtcattg ttcctggtcg tggatgtgcc      7020
attccaaatc gtcctggtat ttttgtccga gtagcatatt atgcaaaatg gatacacaaa     7080
attattttaa catataaggt accacagtca tag                                   7113
```

<210> SEQ ID NO 3
<211> LENGTH: 34
<212> TYPE: DNA
<213> ORGANISM: Artificial Sequence
<220> FEATURE:
<223> OTHER INFORMATION: gHGF3 primer
<400> SEQUENCE: 3
gtaaaggacg cgtctacaag ggaacagtat ctat      34

<210> SEQ ID NO 4
<211> LENGTH: 27
<212> TYPE: DNA
<213> ORGANISM: Artificial Sequence
<220> FEATURE:
<223> OTHER INFORMATION: gHGF4 primer
<400> SEQUENCE: 4
actggatcct ctcggccata aacatct      27

<210> SEQ ID NO 5
<211> LENGTH: 34
<212> TYPE: DNA
<213> ORGANISM: Artificial Sequence
<220> FEATURE:
<223> OTHER INFORMATION: gHGF10 primer
<400> SEQUENCE: 5
gaagcttagc accatgtggg tgaccaaact cctg      34

<210> SEQ ID NO 6
<211> LENGTH: 27
<212> TYPE: DNA
<213> ORGANISM: Artificial Sequence
<220> FEATURE:

<223> OTHER INFORMATION: gHGF5 primer

<400> SEQUENCE: 6
tggccgagag gatccagtat attaata                                    27

<210> SEQ ID NO 7
<211> LENGTH: 27
<212> TYPE: DNA
<213> ORGANISM: Artificial Sequence
<220> FEATURE:
<223> OTHER INFORMATION: gHGF7 primer

<400> SEQUENCE: 7
cccctcgagg atttcgacag tagtttt                                    27

<210> SEQ ID NO 8
<211> LENGTH: 28
<212> TYPE: DNA
<213> ORGANISM: Artificial Sequence
<220> FEATURE:
<223> OTHER INFORMATION: gHGF12 primer

<400> SEQUENCE: 8
gggatccctt cctttctacc tgtatttg                                   28

<210> SEQ ID NO 9
<211> LENGTH: 25
<212> TYPE: DNA
<213> ORGANISM: Artificial Sequence
<220> FEATURE:
<223> OTHER INFORMATION: gHGF13 primer

<400> SEQUENCE: 9
gggatcctgg gtaaacacat ttgaa                                      25

<210> SEQ ID NO 10
<211> LENGTH: 28
<212> TYPE: DNA
<213> ORGANISM: Artificial Sequence
<220> FEATURE:
<223> OTHER INFORMATION: gHGF6 primer

<400> SEQUENCE: 10
gggatcctta tgtttcagac aacttcga                                   28

<210> SEQ ID NO 11
<211> LENGTH: 34
<212> TYPE: DNA
<213> ORGANISM: Artificial Sequence
<220> FEATURE:
<223> OTHER INFORMATION: gHGF1 primer

<400> SEQUENCE: 11
gaagcttgcc accatgtggg tgaccaaact cctg                            34

<210> SEQ ID NO 12
<211> LENGTH: 34
<212> TYPE: DNA
<213> ORGANISM: Artificial Sequence
<220> FEATURE:
<223> OTHER INFORMATION: gHGF2 primer

<400> SEQUENCE: 12
gggatccaga acgcgtcctt taccgatgat gcag                            34

```
<210> SEQ ID NO 13
<211> LENGTH: 35
<212> TYPE: DNA
<213> ORGANISM: Artificial Sequence
<220> FEATURE:
<223> OTHER INFORMATION: gHGF8 primer

<400> SEQUENCE: 13
gggatccctt ctcgagactt gaaagattat gaagc                              35

<210> SEQ ID NO 14
<211> LENGTH: 32
<212> TYPE: DNA
<213> ORGANISM: Artificial Sequence
<220> FEATURE:
<223> OTHER INFORMATION: gHGF9 primer

<400> SEQUENCE: 14
gtctagagcg gccgctatga ctgtggtacc tt                                 32

<210> SEQ ID NO 15
<211> LENGTH: 36
<212> TYPE: DNA
<213> ORGANISM: Artificial Sequence
<220> FEATURE:
<223> OTHER INFORMATION: cHGF5 primer

<400> SEQUENCE: 15
ggatccacgc gtagcagcac catgtgggtg accaaa                             36

<210> SEQ ID NO 16
<211> LENGTH: 36
<212> TYPE: DNA
<213> ORGANISM: Artificial Sequence
<220> FEATURE:
<223> OTHER INFORMATION: cHGF3 primer

<400> SEQUENCE: 16
ggatcctcta gattacttca gctatgactg tggtac                             36

<210> SEQ ID NO 17
<211> LENGTH: 26
<212> TYPE: DNA
<213> ORGANISM: Artificial Sequence
<220> FEATURE:
<223> OTHER INFORMATION: GHGF5' primer

<400> SEQUENCE: 17
caaatgtcag ccctggagtt ccatga                                        26

<210> SEQ ID NO 18
<211> LENGTH: 23
<212> TYPE: DNA
<213> ORGANISM: Artificial Sequence
<220> FEATURE:
<223> OTHER INFORMATION: GHGF3' primer

<400> SEQUENCE: 18
ctggattgct tgtgaaacag ggt                                           23

<210> SEQ ID NO 19
<211> LENGTH: 4679
<212> TYPE: DNA
<213> ORGANISM: Artificial Sequence
<220> FEATURE:
<223> OTHER INFORMATION: HGF-X6 gene
```

<400> SEQUENCE: 19

```
atgtgggtga ccaaactcct gccagccctg ctgctgcagc atgtcctcct gcatctcctc      60
ctgctcccca tcgccatccc ctatgcagag ggacaaagga aaagaagaaa tacaattcat     120
gaattcaaaa aatcagcaaa gactacccta atcaaaatag atccagcact gaagataaaa     180
accaaaaaag tgaatactgc agaccaatgt gctaatagat gtactaggaa taaaggactt     240
ccattcactt gcaaggcttt tgtttttgat aaagcaagaa acaatgcct ctggttcccc      300
ttcaatagca tgtcaagtgg agtgaaaaaa gaatttggcc atgaatttga cctctatgaa     360
aacaaagact acattagaaa ctgcatcatc ggtaaaggac gcagctacaa gggaacagta     420
tctatcacta gagtggcat caaatgtcag ccctggagtt ccatgatacc acacgaacac      480
aggtaagaac agtatgaaga aaagagatga agcctctgtc ttttttacat gttaacagtc     540
tcatattagt ccttcagaat aattctacaa tcctaaaata acttagccaa cttgctgaat     600
tgtattacgg caaggtttat atgaattcat gactgatatt tagcaaatga ttaattaata     660
tgttaataaa atgtagccaa acaatatct taccttaatg cctcaatttg tagatctcgg      720
tatttgtgga tcccttcctt tctacctgta tttgtcctaa taaattgttg acttattaat     780
tcactacttc ctcacagctt ttttttggct ttacaaatcc actggaaagg tatatgggtg     840
tatcactttg tgtatttcgg tgtgcatgtg tagagggggac aaaaatcctc tctcaaacta    900
taaatattga gtatttgtgt attgaacatt tgctataact actaggtttc ttaaataatc    960
ttaatatata aaatgatata gaaaagggga aattatagtt cgtattattc atctaagtga    1020
agagattaaa acccagggag taaataaatt gtctaaggac taaggttgta tactatttag   1080
gtgatagata tggggcaacc gtatgggttt tatgattaac aaataaactt ctcaccactc   1140
taccatatca actttctccat aaaagagagc tatagtattc tttgcttaaa taaatttgat   1200
tagtgcatga cttcttgaaa acatataaag caaaagtcac atttgattct atcagaaaag   1260
tgagtaagcc atggcccaaa caaaagatgc attaaaatat tctggaatga tggagctaaa   1320
agtaagaaaa atgacttttt aaaaaagttt actgttagga attgtgaaat tatgctgaat   1380
tttagttgca ttataatttt tgtcagtcat acggtctgac aacctgtctt atttctattt   1440
ccccatatga ggaatgctag ttaagtatgg atattaacta ttactactta gatgcattga   1500
agttgcataa tatggataat acttcactgg ttccctgaaa atgtttagtt agtaataagt   1560
ctcttacact atttgttttg tccaataatt tatattttct gaagacttaa ctctagaata   1620
cactcatgtc aaaatgaaag aatttcattg caaaatattg cttggtacat gacgcatacc   1680
tgtatttgtt ttgtgtcaca acatgaaaaa tgatggttta ttagaagttt cattgggtag   1740
gaaacacatt tgaatggtat ttactaagat actaaaatcc ttggacttca ctctaatttt   1800
agtgccattt agaactcaag gtctcagtaa aagtagaaat aaagcctgtt aacaaaacac   1860
aagctgaata ttaaaaatgt aactggattt tcaaagaaat gtttactggt attacctgta   1920
gatgtatatt ctttattatg atcttttgtg taaagtctgg cagacaaatg caatatctaa   1980
ttgttgagtc caatatcaca agcagtacaa agtataaaa aagacttggc cttttctaat    2040
gtgttaaaat actttatgct ggtaataaca ctaagagtag ggcactagaa attttaagtg   2100
aagataatgt gttgcagtta ctgcactcaa tggcttacta ttataaacca aaactgggat   2160
cactaagctc cagtcagtca aaatgatcaa aattattgaa gagaataagc aattctgttc   2220
tttattagga cacagtagat acagactaca aagtggagtg tgcttaataa gaggtagcat   2280
ttgttaagtg tcaattactc tattatccct tggagcttct caaaataacc atataaggtg   2340
```

```
taagatgtta aaggttatgg ttacactcag tgcacaggta agctaatagg ctgagagaag   2400
ctaaattact tactggggtc tcacagtaag aaagtgagct gaagtttcag cccagattta   2460
actggattct gggctctttta ttcatgttac ttcatgaatc tgtttctcaa ttgtgcagaa   2520 aaaaggggc tatttataag aaaagcaata acaaacaag taatgatctc aaataagtaa    2580
tgcaagaaat agtgagattt caaaatcagt ggcagcgatt tctcagttct gtcctaagtg   2640
gccttgctca atcacctgct atcttttagt ggagctttga attatgttt cagacaactt   2700 cgattcagtt ctagaatgtt tgactcagca aattcacagg ctcatctttc taacttgatg   2760
gtgaatatgg aaattcagct aaatggatgt taataaaatt caaacgtttt aaggacagat   2820
gaaaatgaca gaattttaag gtaaaatata tgaaggaata taagataaag gatttttcta   2880
ccttcagcaa aaacataccc actaattagt aaaattaata ggcaaaaaaa agttgcatgc   2940
tcttatactg taatgattat catttttaaaa ctagcttttt gccttcgagc tatcggggta   3000
aagacctaca ggaaaactac tgtcgaaatc ctcgagggga agaaggggga ccctggtgtt   3060
tcacaagcaa tccagaggta cgctacgaag tctgtgacat tcctcagtgt tcagaagttg   3120
aatgcatgac ctgcaatggg gagagttatc gaggtctcat ggatcataca gaatcaggca   3180
agatttgtca gcgctgggat catcagacac acaccggca caaattcttg cctgaaagat   3240
atcccgacaa gggctttgat gataattatt gccgcaatcc cgatggccag ccgaggccat   3300
ggtgctatac tcttgaccct cacacccgct gggagtactg tgcaattaaa acatgcgctg   3360
acaatactat gaatgacact gatgttcctt tggaaacaac tgaatgcatc caaggtcaag   3420
gagaaggcta caggggcact gtcaatacca tttggaatgg aattccatgt cagcgttggg   3480
attctcagta tcctcacgag catgacatga ctcctgaaaa tttcaagtgc aaggacctac   3540
gagaaaatta ctgccgaaat ccagatgggt ctgaatcacc ctggtgtttt accactgatc   3600
caaacatccg agttggctac tgctcccaaa ttccaaactg tgatatgtca catggacaag   3660
attgttatcg tgggaatggc aaaaattata tgggcaactt atcccaaaca agatctggac   3720
taacatgttc aatgtgggac aagaacatgg aagacttaca tcgtcatatc ttctgggaac   3780
cagatgcaag taagctgaat gagaattact gccgaaatcc agatgatgat gctcatggac   3840
cctggtgcta cacgggaaat ccactcattc cttgggatta ttgccctatt tctcgttgtg   3900
aaggtgatac cacacctaca atagtcaatt tagaccatcc cgtaatatct tgtgccaaaa   3960
cgaaacaatt gcgagttgta atgggattc caacacgaac aaacatagga tggatgttta   4020
gtttgagata cagaaataaa catatctgcg gaggatcatt gataaaggag agttgggttc   4080
ttactgcacg acagtgtttc ccttctcgag acttgaaaga ttatgaagct tggcttggaa   4140
ttcatgatgt ccacggaaga ggagatgaga atgcaaaca ggttctcaat gtttcccagc   4200
tggtatatgg ccctgaagga tcagatctgg ttttaatgaa gcttgccagg cctgctgtcc   4260
tggatgattt tgttagtacg attgatttac ctaattatgg atgcacaatt cctgaaaaga   4320
ccagttgcag tgtttatggc tggggctaca ctggattgat caactatgat ggcctattac   4380
gagtggcaca tctctatata atgggaaatg agaaatgcag ccagcatcat cgagggaagg   4440
tgactctgaa tgagtctgaa atatgtgctg gggctgaaaa gattggatca ggaccatgtg   4500 aggggggatta tggtggccca cttgtttgtg agcaacataa aatgagaatg gttcttggtg   4560
tcattgttcc tggtcgtgga tgtgccattc caaatcgtcc tggtatttttt gtccgagtag   4620 catattatgc aaaaatggata cacaaaatta ttttaacata taaggtacca cagtcatag   4679
```

<210> SEQ ID NO 20
<211> LENGTH: 3679
<212> TYPE: DNA
<213> ORGANISM: Artificial Sequence
<220> FEATURE:
<223> OTHER INFORMATION: HGF-X7 gene

<400> SEQUENCE: 20

| | | | | | |
|---|---|---|---|---|---|
| atgtgggtga | ccaaactcct | gccagccctg | ctgctgcagc | atgtcctcct | gcatctcctc | 60 |
| ctgctcccca | tcgccatccc | ctatgcagag | ggacaaagga | aaagaagaaa | tacaattcat | 120 |
| gaattcaaaa | aatcagcaaa | gactacccta | atcaaaatag | atccagcact | gaagataaaa | 180 |
| accaaaaaag | tgaatactgc | agaccaatgt | gctaatagat | gtactaggaa | taaaggactt | 240 |
| ccattcactt | gcaaggcttt | tgttttttgat | aaagcaagaa | acaatgcct | ctggttcccc | 300 |
| ttcaatagca | tgtcaagtgg | agtgaaaaaa | gaatttggcc | atgaatttga | cctctatgaa | 360 |
| aacaaagact | acattagaaa | ctgcatcatc | ggtaaaggac | gcagctacaa | gggaacagta | 420 |
| tctatcacta | agagtggcat | caaatgtcag | ccctggagtt | ccatgatacc | acacgaacac | 480 |
| aggtaagaac | agtatgaaga | aaagagatga | agcctctgtc | tttttttacat | gttaacagtc | 540 |
| tcatattagt | ccttcagaat | aattctacaa | tcctaaaata | acttagccaa | cttgctgaat | 600 |
| tgtattacgg | caaggtttat | atgaattcat | gactgatatt | tagcaaatga | ttaattaata | 660 |
| tgttaataaa | atgtagccaa | acaatatct | taccttaatg | cctcaatttg | tagatctcgg | 720 |
| tatttgtgga | tcctgggtag | gaaacacatt | tgaatggtat | ttactaagat | actaaaatcc | 780 |
| ttggacttca | ctctaatttt | agtgccattt | agaactcaag | gtctcagtaa | agtagaaat | 840 |
| aaagcctgtt | aacaaaacac | aagctgaata | ttaaaaatgt | aactggattt | tcaaagaaat | 900 |
| gtttactggt | attacctgta | gatgtatatt | ctttattatg | atcttttgtg | taaagtctgg | 960 |
| cagacaaatg | caatatctaa | ttgttgagtc | caatatcaca | agcagtacaa | agtataaaa | 1020 |
| aagacttggc | ctttttctaat | gtgttaaaat | actttatgct | ggtaataaca | ctaagagtag | 1080 |
| ggcactagaa | atttttaagtg | aagataatgt | gttgcagtta | ctgcactcaa | tggcttacta | 1140 |
| ttataaacca | aaactgggat | cactaagctc | cagtcagtca | aaatgatcaa | aattattgaa | 1200 |
| gagaataagc | aattctgttc | tttattagga | cacagtagat | acagactaca | agtggagtg | 1260 |
| tgcttaataa | gaggtagcat | ttgttaagtg | tcaattactc | tattatccct | tggagcttct | 1320 |
| caaaataacc | atataaggtg | taagatgtta | aaggttatgg | ttacactcag | tgcacaggta | 1380 |
| agctaatagg | ctgagagaag | ctaaattact | tactggggtc | tcacagtaag | aaagtgagct | 1440 |
| gaagtttcag | cccagattta | actggattct | gggctcttta | ttcatgttac | ttcatgaatc | 1500 |
| tgtttctcaa | ttgtgcagaa | aaaagggggc | tatttataag | aaaagcaata | aacaaacaag | 1560 |
| taatgatctc | aaataagtaa | tgcaagaaat | agtgagattt | caaaatcagt | ggcagcgatt | 1620 |
| tctcagttct | gtcctaagtg | gccttgctca | atcacctgct | atcttttagt | ggagctttga | 1680 |
| aattatgttt | cagacaactt | cgattcagtt | ctagaatgtt | tgactcagca | aattcacagg | 1740 |
| ctcatctttc | taacttgatg | gtgaatatgg | aaattcagct | aaatggatgt | taataaaatt | 1800 |
| caaacgtttt | aaggacagat | gaaaatgaca | gaattttaag | gtaaaatata | tgaaggaata | 1860 |
| taagataaag | gattttccta | ccttcagcaa | aaacataccc | actaattagt | aaaattaata | 1920 |
| ggcaaaaaaa | agttgcatgc | tcttatactg | taatgattat | cattttaaaa | ctagcttttt | 1980 |
| gccttcgagc | tatcggggta | aagacctaca | ggaaaactac | tgtcgaaatc | ctcgagggga | 2040 |
| agaaggggga | ccctggtgtt | tcacaagcaa | tccagaggta | cgctacgaag | tctgtgacat | 2100 |

```
tcctcagtgt tcagaagttg aatgcatgac ctgcaatggg gagagttatc gaggtctcat    2160
ggatcataca gaatcaggca agatttgtca gcgctgggat catcagacac cacaccggca    2220
caaattcttg cctgaaagat atcccgacaa gggctttgat gataattatt gccgcaatcc    2280
cgatggccag ccgaggccat ggtgctatac tcttgaccct cacacccgct gggagtactg    2340
tgcaattaaa acatgcgctg acaatactat gaatgacact gatgttcctt ggaaacaac    2400 tgaatgcatc caaggtcaag gagaaggcta caggggcact gtcaatacca tttggaatgg    2460
aattccatgt cagcgttggg attctcagta tcctcacgag catgacatga ctcctgaaaa    2520
tttcaagtgc aaggacctac gagaaaatta ctgccgaaat ccagatgggt ctgaatcacc    2580
ctggtgtttt accactgatc aaacatccg agttggctac tgctcccaaa ttccaaactg    2640
tgatatgtca catggacaag attgttatcg tgggaatggc aaaaattata tgggcaactt    2700
atcccaaaca agatctggac taacatgttc aatgtgggac aagaacatgg aagacttaca    2760
tcgtcatatc ttctgggaac cagatgcaag taagctgaat gagaattact gccgaaatcc    2820
agatgatgat gctcatggac cctggtgcta cacgggaaat ccactcattc cttgggatta    2880
ttgccctatt tctcgttgtg aaggtgatac cacacctaca atagtcaatt tagaccatcc    2940
cgtaatatct tgtgccaaaa cgaaacaatt gcgagttgta atgggattc caacacgaac    3000 aaacatagga tggatggtta gtttgagata cagaaataaa catatctgcg gaggatcatt    3060
gataaaggag agttgggttc ttactgcacg acagtgtttc ccttctcgag acttgaaaga    3120
ttatgaagct tggcttggaa ttcatgatgt ccacggaaga ggagatgaga atgcaaaca    3180 ggttctcaat gtttcccagc tggtatatgg ccctgaagga tcagatctgg ttttaatgaa    3240
gcttgccagg cctgctgtcc tggatgattt tgttagtacg attgatttac ctaattatgg    3300
atgcacaatt cctgaaaaga ccagttgcag tgtttatggc tggggctaca ctggattgat    3360
caactatgat ggcctattac gagtggcaca tctctatata tgggaaatg agaaatgcag    3420 ccagcatcat cgagggaagg tgactctgaa tgagtctgaa atatgtgctg gggctgaaaa    3480
gattggatca ggaccatgtg aggggattga tggtggccca cttgtttgtg agcaacataa    3540
aatgagaatg gttcttggtg tcattgttcc tggtcgtgga tgtgccattc caaatcgtcc    3600
tggtattttt gtccgagtag catattatgc aaaatgata cacaaaatta ttttaacata    3660
taaggtacca cagtcatag                                                3679

<210> SEQ ID NO 21
<211> LENGTH: 2729
<212> TYPE: DNA
<213> ORGANISM: Artificial Sequence
<220> FEATURE:
<223> OTHER INFORMATION: HGF-X8 gene

<400> SEQUENCE: 21
atgtgggtga ccaaactcct gccagccctg ctgctgcagc atgtcctcct gcatctcctc      60
ctgctcccca tcgccatccc ctatgcagag ggacaaagga aagaagaaa tacaattcat     120 gaattcaaaa aatcagcaaa gactacccta atcaaaatag atccagcact gaagataaaa     180
accaaaaaag tgaatactgc agaccaatgt gctaatagat gtactaggaa taaaggactt     240
ccattcactt gcaaggcttt tgttttttgat aaagcaagaa acaatgcct ctggttcccc     300 ttcaatagca tgtcaagtgg agtgaaaaaa gaatttggcc atgaatttga cctctatgaa     360
aacaaagact acattagaaa ctgcatcatc ggtaaaggac gcagctacaa gggaacagta     420
```

```
tctatcacta agagtggcat caaatgtcag ccctggagtt ccatgatacc acacgaacac    480
aggtaagaac agtatgaaga aaagagatga agcctctgtc ttttttacat gttaacagtc    540
tcatattagt ccttcagaat aattctacaa tcctaaaata acttagccaa cttgctgaat    600
tgtattacgg caaggtttat atgaattcat gactgatatt tagcaaatga ttaattaata    660
tgttaataaa atgtagccaa acaatatct taccttaatg cctcaatttg tagatctcgg     720
tatttgtgga tccttatgtt tcagacaact tcgattcagt tctagaatgt ttgactcagc    780
aaattcacag gctcatcttt ctaacttgat ggtgaatatg gaaattcagc taaatggatg    840
ttaataaaat tcaaacgttt taaggacaga tgaaaatgac agaatttta ggtaaaatat     900 atgaaggaat ataagataaa ggattttct accttcagca aaacatacc cactaattag      960 taaaattaat aggcaaaaaa aagttgcatg ctcttatact gtaatgatta tcattttaaa   1020
actagctttt tgccttcgag ctatcggggt aaagacctac aggaaaacta ctgtcgaaat   1080
cctcgagggg aagaaggggg accctggtgt tcacaagca atccagaggt acgctacgaa    1140
gtctgtgaca ttcctcagtg ttcagaagtt gaatgcatga cctgcaatgg ggagagttat   1200
cgaggtctca tggatcatac agaatcaggc aagatttgtc agcgctggga tcatcagaca   1260
ccacaccggc acaaattctt gcctgaaaga tatcccgaca agggctttga tgataattat   1320
tgccgcaatc ccgatggcca gccgaggcca tggtgctata ctcttgaccc tcacaccgc    1380 tgggagtact gtgcaattaa acatgcgct gacaatacta tgaatgacac tgatgttcct    1440
ttggaaacaa ctgaatgcat ccaaggtcaa ggagaaggct acaggggcac tgtcaatacc   1500
atttggaatg gaattccatg tcagcgttgg gattctcagt atcctcacga gcatgacatg   1560
actcctgaaa atttcaagtg caaggaccta cgagaaaatt actgccgaaa tccagatggt   1620
ctgaatcacc ctggtgtttt accactgatc caaacatccg agttggctac tgctcccaaa   1680
ttccaaactg tgatatgtca catggacaag attgttatcg tgggaatggc aaaaattata   1740
tgggcaactt atcccaaaca agatctggac taacatgttc aatgtgggac aagaacatgg   1800
aagacttaca tcgtcatatc ttctgggaac cagatgcaag taagctgaat gagaattact   1860
gccgaaatcc agatgatgat gctcatggac cctggtgcta cacgggaaat ccactcattc   1920
cttgggatta ttgccctatt tctcgttgtg aaggtgatac cacacctaca atagtcaatt   1980
tagaccatcc cgtaatatct tgtgccaaaa cgaaacaatt gcgagttgta atgggattc    2040 caacacgaac aaaacatagga tggatggtta gtttgagata cagaaataaa catatctgcg   2100
gaggatcatt gataaaggag agttgggttc ttactgcacg acagtgtttc ccttctcgag   2160
acttgaaaga ttatgaagct tggcttggaa ttcatgatgt ccacggaaga ggagatgaga   2220
aatgcaaaca ggttctcaat gtttcccagc tggtatatgg ccctgaagga tcagatctgg   2280
ttttaatgaa gcttgccagg cctgctgtcc tggatgattt tgttagtacg attgatttac   2340
ctaattatgg atgcacaatt cctgaaaaga ccagttgcag tgtttatggc tggggctaca   2400
ctggattgat caactatgat ggcctattac gagtggcaca tctctatata tgggaaatg    2460 agaaatgcag ccagcatcat cgagggaagg tgactctgaa tgagtctgaa atatgtgctg   2520
gggctgaaaa gattggatca ggaccatgtg aggggggatta tggtggccca cttgtttgtg   2580
agcaacataa aatgagaatg gttcttggtg tcattgttcc tggtcgtgga tgtgccattc   2640
caaatcgtcc tggtattttt gtccgagtag catattatgc aaaatggata cacaaaatta   2700
ttttaacata taaggtacca cagtcatag                                     2729
```